US007807455B2

(12) United States Patent
Grobler et al.

(10) Patent No.: US 7,807,455 B2
(45) Date of Patent: Oct. 5, 2010

(54) METHOD TO CONFER CELL CULTURE REPLICATION ACTIVITY TO DIFFERENT HEPATITIS C VIRUS ISOLATES

(75) Inventors: Jay Grobler, Gwynedd, PA (US); Osvaldo Flores, North Wales, PA (US); Eric J. Markel, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 702 days.

(21) Appl. No.: 10/543,633

(22) PCT Filed: Feb. 9, 2004

(86) PCT No.: PCT/US2004/003726

§ 371 (c)(1),
(2), (4) Date: Jul. 28, 2005

(87) PCT Pub. No.: WO2004/074507

PCT Pub. Date: Sep. 2, 2004

(65) Prior Publication Data

US 2006/0228697 A1    Oct. 12, 2006

Related U.S. Application Data

(60) Provisional application No. 60/447,318, filed on Feb. 13, 2003.

(51) Int. Cl.
*C12N 15/00* (2006.01)
*C12Q 1/68* (2006.01)
*C12Q 1/70* (2006.01)
*C07H 21/00* (2006.01)

(52) U.S. Cl. .................. 435/320.1; 435/5; 435/6; 536/23.72

(58) Field of Classification Search ................ None
See application file for complete search history.

(56) References Cited

U.S. PATENT DOCUMENTS

| 5,739,002 | A | 4/1998 | De Francesco et al. |
| 6,630,343 | B1 | 10/2003 | Bartenschlager |
| 2002/0155133 | A1 | 10/2002 | Bichko |

FOREIGN PATENT DOCUMENTS

| WO | WO 96/37619 | 11/1996 |
| WO | WO 01/89364 | 11/2001 |
| WO | WO 02/38793 | 5/2002 |
| WO | WO 02/052015 | 7/2002 |
| WO | WO 02/059321 | 8/2002 |

OTHER PUBLICATIONS

Bowie et al., "Deciphering the Message in Protein Sequences: Tolerance to Amino Acid Substitutions," Science, vol. 247, No. 4948. (Mar. 16, 1990), pp. 1306-1310.*
Behrens, S. et al. "Identification and properties of the RNA-dependent RNA polymerase of hepatitis C virus", The EMBO Journal, 1996, vol. 15, pp. 12-22.
Bukh, J. et al. "Mutations that permit efficient replication of hepatitis C virus RNA in Huh-7 cells prevent productive replication in chimpanzees", Proc. Natl. Acad. Sci. USA, 2002, vol. 99, pp. 14416-14421.
Grobler, J. et al. "Identification of a Key Determinant of Hepatitis C Virus Cell Culture Adaptation in Domain II of NS3 Helicase", The Journal of Biological Chemistry, 2003, vol. 278, pp. 16741-16746.
Bartenschlager, R. et al. "Nonstructural Protein 3 of the Hepatitis C Virus Encodes a Serine-Type Proteinase Required for Cleavage at the NS3/4 and NS4/5 Junctions", Journal of Virology, 1993, vol. 67, pp. 3835-3844.
Blight, K. et al. "Efficient Initiation of HCV RNA Replication in Cell Culture", Science, 2000, vol. 290, pp. 1972-1974.
Chamberlain, R. et al. "Complete nucleotide sequence of a type 4 hepatitis C virus variant, the predominant genotype in the Middle East", Journal of General Virology, 1997, vol. 78, pp. 1341-1347.
Choo, Q. et al. "Isolation of a cDNA Clone Derived from a Blood-Borne Non-A, Non-B Viral Hepatitis Genome", Science, 1989, vol. 244, p. 359-362.
De Francesco, R. et al. "Biochemical and Immunological Properties of the Nonstructural Proteins of the Hepatitis C Virus: Implications for Development for Antiviral Agents and Vaccines", Seminars in Liver Disease, 2000, vol. 20, pp. 69-83.
Failla, C. et al. "Both NS3 and NS4A Are Required for Proteolytic Processing of Hepatitis C Virus Nonstructual Proteins", Journal of Virology, 1994, vol. 68, pp. 3753-3760.
Farci, P. et al. "Clinical Significance of Hepatitis C Virus Genotypes and Quasispecies", Seminars in Liver Disease, 2000, vol. 20, pp. 103-126.
Guo, J. et al. "Effect of Alpha Interferon on the Hepatitis C Virus Replicon", Journal of Virology, 2001, vol. 75, pp. 8516-8523.
Grakoui, A. et al. "A second hepatitis C virus-encoded proteinase", Proc. Natl. Acad. Sci. USA, 1993, vol. 90, pp. 10583-10587.
Grakoui, A. et al. "Expression and Identification of Hepatitis C Virus Polyprotein Cleavage Products", Journal of Virology, 1993, vol. 67, pp. 1385-1395.
Hijikata, M. et al. "Proteolytic processing and membrane association of putative nonstructural proteins of hepatitis C virus", Proc. Natl. Acad. Sci. USA, 1993, vol. 90,. pp. 10773-10777.
Honda, M. et al. "Structural Requirements for Initiation of Translation by Internal Ribosome Entry within Genome-Length Hepatitis C Virus RNA", Virology, 1996, vol. 222, pp. 31-42.
Hong, Z. et al. "Generation of Transmissible Hepatitis C Virions from a Molecular Clone in Chimpanzees", Virology, 1999, vol. 256, pp. 36-44.
Ikeda, M. et al. "Selectable Subgenomic and Genome-Length Dicistronic RNAs Derived from an Infectious Molecular Clone of the HCV-N Strain of Hepatitis C Virus Replicate Efficiently in Cultured Huh7 Cells", Journal of Virology, 2002, vol. 76, pp. 2997-3006.

(Continued)

*Primary Examiner*—Zachariah Lucas
(74) *Attorney, Agent, or Firm*—Melissa B. Wenk; Sheldon O. Heber

(57) ABSTRACT

The present invention features methods for producing HCV replicons using HCV encoding sequences from different isolates. The featured methods are based on the discovered importance of NS3 amino acid position 470 in conferring cell culture replication activity to different HCV isolates.

18 Claims, 12 Drawing Sheets

OTHER PUBLICATIONS

Kolykhalov, A. et al. "Hepatitis C Virus-Encoded Enzymatic Activities and Conserved RNA Elements in the 3' Nontranslated Region Are Essential for Virus Replication in Vivo", Journal of Virology, 2000, vol. 74, pp. 2046-2051.

Kolykhalov, A. et al. "Identification of a Highly Conserved Sequence Element at the 3' Terminus of Hepatitis C Virus Genome RNA", Journal of Virology, 1996, vol. 70, pp. 3363-3371.

Kolykhalov, A. et al. "Transmission of Hepatitis C Intrahepatic Inoculation with Transcribed RNA", Science, 1997, vol. 277, pp. 570-574.

Krieger, N. et al. "Enhancement of Hepatitis C Virus RNA Replication by Cell Culture-Adaptive Mutations", Journal of Virology, 2001, vol. 75, pp. 4614-4624.

Kuo, G. et al. "An Assay for Circulating Antibodies to a Major Etiologic Virus of Human Non-A, Non-B Hepatitis", Science, 1989, Vo. 244, pp. 362-364.

Lohmann, V. et al. "Biochemical and Kinetic Analyses of NS5B RNA-Dependent Polymerase of the Hepatitis C Virus", Virology, 1998, vol. 249, pp. 108-118.

Lohmann, V. et al. "Mutations in Hepatitis C Virus RNAs Conferring Cell Culture Adaptation", Journal of Virology, 2001, vol. 75, pp. 1437-1449.

Lohmann, V. et al. "Replication of Subgenomic Hepatitis C Virus RNAs in a Hepatoma Cell Line", Science, 1999, Vo. 285, p. 110-113.

Mizushima, H. et al. "Analysis of N-Terminal Processing of Hepatitis C Virus Nonstructural Protein 2", Journal of Virology, 1994, vol. 68, pp. 2731-2734.

Mottola, G. et al. "Hepatitis C Virus Nonstructural Proteins Are Localized in a Modified Endoplasmic Reticulum of Cells Expressing Viral Subgenomic Replicons", Virology, 2002, vol. 293, pp. 31-43.

Pawlotsky, J. "Hepatitis C virus (HCV) NS5A protein: role in HCV replication and resistance to interferon-$\alpha$", Journal of Viral Hepatitis 1999, vol. 6, (Suppl. 1), pp. 47-48.

Pietschmann, T. et al. "Characterization of Cell Lines Carrying Self-Replicating Hepatitis C Virus RNAs", of Virology, 2001, vol. 75, pp. 1252-1264.

Simmonds, P. et al. "The origin and evolution of hepatitis viruses in humans", Journal of General Virology, 2001, vol. 82, pp. 693-712.

Takamizawa, A. et al. "Structure and Organization of the Hepatitis C Virus Genome Isolated from Human Carriers", Journal of Virology, 1991, vol. 65, pp. 1105-1113.

Tanaka, T. et al. "Structure of the 3' Terminus of the Hepatitis C Virus Genome", Journal of Virology, 1996, vol. 70, pp. 3307-3312.

Tomei, L. et al. "NS3 Is a Serine Protease Required for Processing of Hepatitis C Virus Polyprotein", Journal of Virology, 1993, vol. 67, pp. 4017-4026.

Walsh, A. et al. "Epidemiology of Hepatitis C: Geographic Differences and Temporal Trends", Seminars in Liver Disease, 2000, vol. 20, pp. 1-16.

Yanagi, M. et al. "Transcripts from a single full-length cDNA clone of hepatitis C virus are infectious when directly transfected into the liver of a chimpanzee", Proc. Natl. Acad. Sci. USA, 1997, vol. 94, pp. 8738-8743.

* cited by examiner

```
   1 MAPITAYSQQ TRGLLGCIIT SLTGRDKNQV EGEVQVVSTA TQSFLATCVN GVCWTVYHGA
  61 GSKTLAGPKG PITQMYTNVD QDLVGWQAPP GARSLTPCTC GSSDLYLVTR HADVIPVRRR
 121 GDSRGSLLSP RPVSYLKGSS GGPLLCPSGH AVGIFRAAVC TRGVAKAVDF VPVESMETTM
 181 RSPVFTDNSS PPAVPQSFQV AHLHAPTGSG KSTKVPAAYA AQGYKVLVLN PSVAATLGFG
 241 AYMSKAHGID PNIRTGVRTI TTGAPVTYST YGKFLADGGC SGGAYDIIIC DECHSTDSTT
 301 ILGIGTVLDQ AETAGARLVV LATATPPGSV TVPHPNIEEV ALSNTGEIPF YGKAIPIEAI
 361 RGGRHLIFCH SKKKCDELAA KLSGLGINAV AYYRGLDVSV IPTIGDVVVV ATDALMTGYT
 421 GDFDSVIDCN TCVTQTVDFS LDPTFTIETT TVPQDAVSRS QRRGRTGRGR MGIYRFVTPG
 481 ERPSGMFDSS VLCECYDAGC AWYELTPAET SVRLRAYLNT PGLPVCQDHL EFWESVFTGL
 541 THIDAHFLSQ TKQAGDNFPY LVAYQATVCA RAQAPPPSWD QMWKCLIRLK PTLHGPTPLL
 601 YRLGAVQNEV TLTHPITKYI MACMSADLEV VTSTWVLVGG VLAALAAYCL TTGSVVIVGR
 661 IILSGRPAIV PDREFLYQEF DEMEECASHL PYIEQGMQLA EQFKQKALGL LQTATKQAEA
 721 AAPVVESKWR ALETFWAKHM WNFISGIQYL AGLSTLPGNP AIASLMAFTA SITSPLTTQS
 781 TLLFNILGGW VAAQLAPPSA ASAFVGAGIA GAAVGSIGLG KVLVDILAGY GAGVAGALVA
 841 FKVMSGEMPS TEDLVNLLPA ILSPGALVVG VVCAAILRRH VGPGEGAVQW MNRLIAFASR
 901 GNHVSPTHYV PESDAAARVT QILSSLTITQ LLKRLHQWIN EDCSTPCSGS WLRDVWDWIC
 961 TVLTDFKTWL QSKLLPQLPG VPFFSCQRGY KGVWRGDGIM QTTCPCGAQI TGHVKNGSMR
1021 IVGPKTCSNT WHGTFPINAY TTGPCTPSPA PNYSRALWRV AAEEYVEVTR VGDFHYVTGM
1081 TTDNVKCPCQ VPAPEFFTEV DGVRLHRYAP ACRPLLREEV TFQVGLNQYL VGSQLPCEPE
1141 PDVAVLTSML TDPSHITAET AKRRLARGSP PSLASSSAIQ LSAPSLKATC TTHHVSPDAD
1201 LIEANLLWRQ EMGGNITRVE SENKVVVLDS FDPLRAEEDE REVSVPAEIL RKSKKFPAAM
1261 PIWARPDYNP PLLESWKDPD YVPPVVHGCP LPPIKAPPIP PPRRKRTVVL TESSVSSALA
1321 ELATKTFGSS ESSAVDSGTA TALPDQASDD GDKGSDVESY SSMPPLEGEP GDPDLSDGSW
1381 STVSEEASED VVCCSMSYTW TGALITPCAA EESKLPINAL SNSLLRHHNM VYATTSRSAG
1441 LRQKKVTFDR LQVLDDHYRD VLKEMKAKAS TVKAKLLSVE EACKLTPPHS AKSKFGYGAK
1501 DVRNLSSKAV NHIHSVWKDL LEDTVTPIDT TIMAKNEVFC VQPEKGGRKP ARLIVFPDLG
1561 VRVCEKMALY DVVSTLPQVV MGSSYGFQYS PGQRVEFLVN TWKSKKNPMG FSYDTRCFDS
1621 TVTENDIRVE ESIYQCCDLA PEARQAIKSL TERLYIGGPL TNSKGQNCGY RRCRASGVLT
1681 TSCGNTLTCY LKASAACRAA KLQDCTMLVN GDDLVVICES AGTQEDAASL RVFTEAMTRY
1741 SAPPGDPPQP EYDLELITSC SSNVSVAHDA SGKRVYYLTR DPTTPLARAA WETARHTPVN
1801 SWLGNIIMYA PTLWARMILM THFFSILLAQ EQLEKALDCQ IYGACYSIEP LDLPQIIERL
1861 HGLSAFSLHS YSPGEINRVA SCLRKLGVPP LRAWRHRARN VRARLLSRGG RAAICGKYLF
1921 NWAVRTKLKL TPIAAAGRLD LSSWFTAGYS GGDIYHGVSH ARPRWFWFCL LLLAAGIGIY
1981 LLPNR
```

FIG. 1

```
   1  MAPITAYAQQ  TRGLLGCIIT  SLTGRDKNQV  EGEVQIVSTA  TQTFLATCIN  GVCWTVYHGA
  61  GTRTIASPKG  PVIQMYTNVD  QDLVGWPAPQ  GSRSLTPCTC  GSSDLYLVTR  HADVIPVRRR
 121  GDSRGSLLSP  RPISYLKGSS  GGPLLCPAGH  AVGLFRAAVC  TRGVAKAVDF  IPVENLETTM
 181  RSPVFTDNSS  PPAVPQSFQV  AHLHAPTGSG  KSTKVPAAYA  AQGYKVLVLN  PSVAATLGFG
 241  AYMSKAHGVD  PNIRTGVRTI  TTGSPITYST  YGKFLADGGC  SGGAYDIIIC  DECHSTDATS
 301  ILGIGTVLDQ  AETAGARLVV  LATATPPGSV  TVSHPNIEEV  ALSTTGEIPF  YGKAIPLEVI
 361  KGGRHLIFCH  SKKKCDELAA  KLVALGINAV  AYYRGLDVSV  IPTSGDVVVV  STDALMTGFT
 421  GDFDSVIDCN  TCVTQTVDFS  LDPTFTIETT  TLPQDAVSRT  QRRGRTGRGK  PGIYRFVAPG
 481  ERPSGMFDSS  VLCECYDAGC  AWYELTPAET  TVRLRAYMNT  PGLPVCQDHL  EFWEGVFTGL
 541  THIDAHFLSQ  TKQSGENFPY  LVAYQATVCA  RAQAPPPSWD  QMWKCLIRLK  PTLHGPTPLL
 601  YRLGAVQNEV  TLTHPITKYI  MTCMSADLEV  VTSTWVLVGG  VLAALAAYCL  STGCVVIVGR
 661  IVLSGKPAII  PDREVLYQEF  DEMEECSQHL  PYIEQGMMLA  EQFKQKALGL  LQTASRHAEV
 721  ITPAVQTNWQ  KLEVFWAKHM  WNFISGIQYL  AGLSTLPGNP  AIASLMAFTA  AVTSPLTTGQ
 781  TLLFNILGGW  VAAQLAAPGA  ATAFVGAGLA  GAAIGSVGLG  KVLVDILAGY  GAGVAGALVA
 841  FKIMSGEVPS  TEDLVNLLPA  ILSPGALVVG  VVCAAILRRH  VGPGEGAVQW  MNRLIAFASR
 901  GNHVSPTHYV  PESDAAARVT  AILSSLTVTQ  LLRRLHQWIS  SECTTPCSGS  WLRDIWDWIC
 961  EVLSDFKTWL  KAKLMPQLPG  IPFVSCQRGY  RGVWRGDGIM  HTRCHCGAEI  TGHVKNGTMR
1021  IVGPRTCRNM  WSGTFPINAY  TTGPCTPLPA  PNYKFALWRV  SAEEYVEIRR  VGDFHYVSGM
1081  TTDNLKCPCQ  IPSPEFFTEL  DGVRLHRFAP  PCKPLLREEV  SFRVGLHEYP  VGSQLPCEPE
1141  PDVAVLTSML  TDPSHITAEA  AGRRLARGSP  PSMASSSAIQ  LSAPSLKATC  TANHDSPDAE
1201  LIEANLLWRQ  EMGGNITRVE  SENKVVILDS  FDPLVAEEDE  REVSVPAEIL  RKSRRFARAL
1261  PVWARPDYNP  PLVETWKKPD  YEPPVVHGCP  LPPPRSPPVP  PPRKKRTVVL  TESTLSTALA
1321  ELATKSFGSS  STSGITGDNT  TTSSEPAPSG  CPPDSDVESY  SSMPPLEGEP  GDPDLSDGSW
1381  STVSSGADTE  DVVCCSMSYS  WTGALVTPCA  AEEQKLPINA  LSNSLLRHHN  LVYSTTSRSA
1441  CQRQKKVTFD  RLQVLDSHYQ  DVLKEVKAAA  SKVKANLLSV  EEACSLTPPH  SAKSKFGYGA
1501  KDVRCHARKA  VAHINSVWKD  LLEDSVTPID  TTIMAKNEVF  CVQPEKGGRK  PARLIVFPDL
1561  GVRVCEKMAL  YDVVSKLPLA  VMGSSYGFQY  SPGQRVEFLV  QAWKSKKTPM  GFSYDTRCFD
1621  STVTESDIRT  EEAIYQCCDL  DPQARVAIKS  LTERLYVGGP  LTNSRGENCG  YRRCRASGVL
1681  TTSCGNTLTC  YIKARAACRA  AGLQDCTMLV  CGDDLVVICE  SAGVQEDAAS  LRAFTEAMTR
1741  YSAPPGDPPQ  PEYDLELITS  CSSNVSVAHD  GAGKRVYYLT  RDPTTPLARA  AWETARHTPV
1801  NSWLGNIIMF  APTLWARMIL  MTHFFSVLIA  RDQLEQALNC  EIYGACYSIE  PLDLPPIIQR
1861  LHGLSAFSLH  SYSPGEINRV  AACLRKLGVP  PLRAWRHRAR  SVRARLLSRG  GRAAICGKYL
1921  FNWAVRTKLK  LTPIAAAGRL  DLSGWFTAGY  SGGDIYHSVS  HARPRWFWFC  LLLLAAGVGI
1981  YLLPNR
```

FIG. 2

```
   1    gccagccccc gattgggggc gacactccac catagatcac tccoctgtga ggaactactg
  61    tcttcacgca gaaagcgtct agccatggcg ttagtatgag tgtcgtgcag cctccaggcc
 121    cccccctccc gggagagcca tagtggtctg cggaaccggt gagtacaccg gaattgccag
 181    gacgaccggg tcctttcttg gatcaaccog ctcaatgcct ggagatttgg gcgtgccccc
 241    gcgagactgc tagccgagta gtgttgggtc gcgaaaggcc ttgtggtact gcctgatagg
 301    gtgcttgcga gtgccccggg aggtctcgta gaccgtgcac catgagcacg aatcctaaac
 361    ctcaaagaaa aaccaagggg cgcgccatgc acccagaaac gctggtgaaa gtaaaagatg
 421    ctgaagatca gttgggtgca cgagtgggtt acatcgaact ggatctcaac agcggtaaga
 481    tccttgagag ttttcgcccc gaagaacgtt tccaatgat gagcacttt aaagttctgc
 541    tatgtggcgc ggtattatcc cgtattgacg ccgggcaaga gcaactcggt cgccgcatac
 601    actattctca gaatgacttg gttgagtact caccagtcac agaaaagcat cttacggatg
 661    gcatgacagt aagagaatta tgcagtgctg ccataaccat gagtgataac actgcggcca
 721    acttacttct gacaacgatc ggaggaccga aggagctaac cgcttttttg cacaacatgg
 781    gggatcatgt aactcgcctt gatcgttggg aaccggagct gaatgaagcc ataccaaacg
 841    acgagcgtga caccacgatg cctgtagcaa tggcaacaac gttgcgcaaa ctattaactg
 901    gcgaactact tactctagct tcccggcaac aattaataga ctggatggag gcggataaag
 961    ttgcaggacc acttctgcgc tcggcccttc cggctggctg gtttattgct gataaatctg
1021    gagccggtga gcgtgggtct cgcggtatca ttgcagcact ggggccagat ggtaagccct
1081    cccgtatcgt agttatctac acgacgggga gtcaggcaac tatggatgaa cgaaatagac
1141    agatcgctga gataggtgcc tcactgatta agcattggta agtttaaaca gaccacaacg
1201    gtttccctct agcgggatca attccgcccc tctccctccc cccccctaa cgttactggc
1261    cgaagccgct tggaataagg ccggtgtgcg tttgtctata tgttattttc caccatattg
1321    ccgtcttttg gcaatgtgag ggcccggaaa cctggccctg tcttcttgac gagcattcct
1381    agggttcttt ccctctcgc caaaggaatg caaggtctgt tgaatgtcgt gaaggaagca
1441    gttcctctgg aagcttcttg aagacaaaca acgtctgtag cgacccttg caggcagcgg
1501    aaccccccac ctggcgacag gtgcctctgc ggccaaaagc cacgtgtata agatacacct
1561    gcaaaggcgg cacaacccca gtgccacgtt gtgagttgga tagttgtgga aagagtcaaa
1621    tggctctcct caagcgtatt caacaagggg ctgaaggatg cccagaaggt accccattgt
1681    atgggatctg atctggggcc tcggtgcaca tgctttacat gtgtttagtc gaggttaaaa
1741    aacgtctagg ccccccgaac cacggggacg tggttttcct ttgaaaaaca cgataatacc
1801    atggcgccca tcacggccta ctcccaacag acgcggggcc tacttggttg catcatcact
1861    agccttacag gccgggacaa gaaccaggtc gagggagagg ttcaggtggt ttccaccgca
1921    acacaatcct tcctggcgac ctgcgtcaac ggcgtgtgtt ggaccgttta ccatggtgct
1981    ggctcaaaga ccttagccgg cccaaagggg ccaatcaccc agatgtacac taatgtggac
```

FIG. 3A

```
2041  caggacctcg tcggctggca ggcgccccc ggggcgcgtt ccttgacacc atgcacctgt
2101  ggcagctcag acctttactt ggtcacgaga catgctgacg tcattccggt gcgccggcgg
2161  ggcgacagta gggggagcct gctctccccc aggcctgtct cctacttgaa gggctcttcg
2221  ggtggtccac tgctctgccc ttcggggcac gctgtgggca tcttccgggc tgccgtatgc
2281  acccgggggg ttgcgaaggc ggtggacttt gtgcccgtag agtccatgga aactactatg
2341  cggtctccgg tcttcacgga caactcatcc ccccggccg taccgcagtc atttcaagtg
2401  gcccacctac acgctcccac tggcagcggc aagagtacta aagtgccggc tgcatatgca
2461  gcccaagggt acaaggtgct cgtcctcaat ccgtccgttg ccgctacctt agggtttggg
2521  gcgtatatgt ctaaggcaca cggtattgac cccaacatca gaactggggt aaggaccatt
2581  accacaggcg cccccgtcac atactctacc tatggcaagt tcttgccga tggtggttgc
2641  tctgggggcg cttatgacat cataatatgt gatgagtgcc attcaactga ctcgactaca
2701  atcttgggca tcggcacagt cctggaccaa gcggagacgg ctggagcgcg gcttgtcgtg
2761  ctcgccaccg ctacgcctcc gggatcggtc accgtgccac acccaaacat cgaggaggtg
2821  gccctgtcta atactggaga gatccccttc tatggcaaag ccatccccat tgaagccatc
2881  agggggggaa ggcatctcat tttctgtcat tccaagaaga gtgcgacga gctcgccgca
2941  aagctgtcag gcctcggaat caacgctgtg gcgtattacc ggggctcga tgtgtccgtc
3001  ataccaacta tcggagacgt cgttgtcgtg gcaacagacg ctctgatgac gggctatacg
3061  ggcgactttg actcagtgat cgactgtaac acatgtgtca cccagacagt cgacttcagc
3121  ttggatccca ccttcaccat tgagacgacg accgtgcctc aagacgcagt gtcgcgctcg
3181  cagcggcggg gtaggactgg caggggtagg atgggcatct acaggtttgt gactccggga
3241  gaacggccct cgggcatgtt cgattcctcg gtcctgtgtg agtgctatga cgcgggctgt
3301  gcttggtacg agctcacccc cgccgagacc tcggttaggt tgcgggccta cctgaacaca
3361  ccagggttgc ccgtttgcca ggaccacctg gagttctggg agagtgtctt cacaggcctc
3421  acccacatag atgcacactt cttgtcccag accaagcagg caggagacaa cttcccctac
3481  ctggtagcat accaagccac ggtgtgcgcc agggctcagg ccccacctcc atcatgggat
3541  caaatgtgga agtgtctcat acggctgaaa cctacgctgc acgggccaac accttgctg
3601  tacaggctgg gagccgtcca aaatgaggtc accctcaccc accccataac caaatacatc
3661  atggcatgca tgtcggctga cctggaggtc gtcactagca cctgggtgct ggtgggcgga
3721  gtccttgcag ctctggccgc gtattgcctg acaacaggca gtgtggtcat tgtgggtagg
3781  attatcttgt ccgggaggcc ggctattgtt cccgacaggg agtttctcta ccaggagttc
3841  gatgaaatgg aagagtgcgc ctcgcacctc ccttacatcg agcagggaat gcagctcgcc
3901  gagcaattca gcagaaagc gctcgggtta ctgcaaacag ccaccaaaca gcggaggct
3961  gctgctcccg tggtggagtc caagtggcga gcccttgaga cattctggc gaagcacatg
4021  tggaatttca tcagcgggat acagtactta gcaggcttat ccactctgcc tgggaacccc
```

FIG. 3B

```
4081  gcaatagcat cattgatggc attcacagcc tctatcacca gcccgctcac cacccaaagt
4141  accctcctgt ttaacatctt ggggggggtgg gtggctgccc aactcgcccc ccccagcgcc
4201  gcttcggctt tcgtgggcgc cggcatcgcc ggtgcggctg ttggcagcat aggccttggg
4261  aaggtgcttg tggacattct ggcgggttat ggagcaggag tggccggcgc gctcgtggcc
4321  ttcaaggtca tgagcggcga gatgccctcc accgaggacc tggtcaatct acttcctgcc
4381  atcctctctc ctggcgccct ggtcgtcggg gtcgtgtgtg cagcaatact gcgtcgacac
4441  gtgggtccgg gagaggggggc tgtgcagtgg atgaaccggc tgatagcgtt cgcctcgcgg
4501  ggtaatcatg tttcccccac gcactatgtg cctgagagcg acgccgcagc gcgtgttact
4561  cagatcctct ccagccttac catcactcag ctgctgaaaa ggctccacca gtggattaat
4621  gaagactgct ccacaccgtg ttccggctcg tggctaaggg atgtttggga ctggatatgc
4681  acggtgttga ctgacttcaa gacctggctc cagtccaagc tcctgccgca gctaccggga
4741  gtcccttttt tctcgtgcca acgcgggtac aagggagtct ggcggggaga cggcatcatg
4801  caaaccacct gcccatgtgg agcacagatc accggacatg tcaaaaacgg ttccatgagg
4861  atcgtcgggc ctaagacctg cagcaacacg tggcatggaa cattccccat caacgcatac
4921  accacgggcc cctgcacacc ctctccagcg ccaaactatt ctagggcgct gtggcgggtg
4981  gccgctgagg agtacgtgga ggtcacgcgg gtgggggatt tccactacgt gacgggcatg
5041  accactgaca acgtaaagtg cccatgccag gttccggctc ctgaattctt cacggaggtg
5101  gacggagtgc ggttgcacag gtacgctccg gcgtgcaggc ctctcctacg ggaggaggtt
5161  acattccagg tcgggctcaa ccaatacctg gttgggtcac agctaccatg cgagcccgaa
5221  ccggatgtag cagtgctcac ttccatgctc accgacccct cccacatcac agcagaaacg
5281  gctaagcgta ggttggccag ggggtctccc ccctccttgg ccagctcttc agctatccag
5341  ttgtctgcgc cttccttgaa ggcgacatgc actacccacc atgtctctcc ggacgctgac
5401  ctcatcgagg ccaacctcct gtggcggcag gagatgggcg gaacatcac ccgcgtggag
5461  tcggagaaca aggtggtagt cctggactct ttcgacccgc ttcgagcgga ggaggatgag
5521  agggaagtat ccgttccggc ggagatcctg cggaaatcca agaagttccc cgcagcgatg
5581  cccatctggg cgcgccgga ttacaaccct ccactgttag agtcctggaa ggacccggac
5641  tacgtccctc cggtggtgca cgggtgcccg ttgccaccta tcaaggcccc tccaatacca
5701  cctccacgga gaaagaggac ggttgtccta acagagtcct ccgtgtcttc tgccttagcg
5761  gagctcgcta ctaagaacctt cggcagctcc gaatcatcgg ccgtcgacag cggcacggcg
5821  accgcccttc ctgaccaggc ctccgacgac ggtgacaaag atccgacgt tgagtcgtac
5881  tcctccatgc cccccttga gggggaaccg ggggacccccg atctcagtga cgggtcttgg
5941  tctaccgtga gcgaggaagc tagtgaggat gtcgtctgct gctcaatgtc ctacacatgg
6001  acaggcgcct tgatcacgcc atgcgctgcg gaggaaagca agctgcccat caacgcgttg
6061  agcaactctt tgctgcgcca ccataacatg gtttatgcca caacatctcg cagcgcaggc
```

FIG. 3C

```
6121  ctgcggcaga agaaggtcac ctttgacaga ctgcaagtcc tggacgacca ctaccgggac
6181  gtgctcaagg agatgaaggc gaaggcgtcc acagttaagg ctaaactcct atccgtagag
6241  gaagcctgca agctgacgcc cccacattcg gccaaatcca agtttggcta tggggcaaag
6301  gacgtccgga acctatccag caaggccgtt aaccacatcc actccgtgtg gaaggacttg
6361  ctggaagaca ctgtgacacc aattgacacc accatcatgg caaaaaatga ggttttctgt
6421  gtccaaccag agaaggagg ccgtaagcca gcccgcctta tcgtattccc agatctggga
6481  gtccgtgtat gcgagaagat ggccctctat gatgtggtct ccaccttcc tcaggtcgtg
6541  atgggctcct catacggatt ccagtactct cctgggcagc gagtcgagtt cctggtgaat
6601  acctggaaat caaagaaaaa ccccatgggc ttttcatatg acactcgctg tttcgactca
6661  acggtcaccg agaacgacat ccgtgttgag gagtcaattt accaatgttg tgacttggcc
6721  cccgaagcca gacaggccat aaaatcgctc acagagcggc tttatatcgg ggtcctctg
6781  actaattcaa aagggcagaa ctgcggttat cgccggtgcc gcgcgagcgg cgtgctgacg
6841  actagctgcg gtaacaccct cacatgttac ttgaaggcct ctgcagcctg tcgagctgcg
6901  aagctccagg actgcacgat gctcgtgaac ggagacgacc ttgtcgttat ctgtgaaagc
6961  gcgggaaccc aagaggacgc ggcgagccta cgagtcttca cggaggctat gactaggtac
7021  tctgccccc ccggggaccc gccccaacca gaatacgact tggagctgat aacatcatgt
7081  tcctccaatg tgtcggtcgc ccacgatgca tcaggcaaaa gggtgtacta cctcacccgt
7141  gatcccacca cccccctcgc acgggctgcg tgggaaacag ctagacacac tccagttaac
7201  tcctggctag gcaacattat catgtatgcg cccactttgt gggcaaggat gattctgatg
7261  actcacttct tctccatcct tctagcacag gagcaacttg aaaaagccct ggactgccag
7321  atctacgggg cctgttactc cattgagcca cttgacctac ctcagatcat tgaacgactc
7381  catggcctta gcgcattttc actccatagt tactctccag gtgagatcaa tagggtggct
7441  tcatgcctca ggaaacttgg ggtaccgccc ttgcgagctt ggagacaccg gcccggaat
7501  gtccgcgcta ggcttctgtc cagaggaggc agggctgcca tatgtggcaa gtacctcttc
7561  aactgggcag taaggacaaa gcttaaactc actccaatag cggccgctgg ccggctggac
7621  ttgtccagct ggttcacggc tggctacagc gggggagaca tttatcacgg cgtgtctcat
7681  gcccggcccc gctggttctg gttttgccta ctcctgctcg ctgcaggaat aggcatctac
7741  ctcctcccca atcgatgaag gttggggtaa acactccggc tcttaggcc atttcctgtg
7801  ttttttttt ttttttttt gtttttttc ttttttttt ttttttttc tttttccctt
7861  cttccttttc tcttttttc ttctttaatg gtggctccat cttagcccta gtcacggcta
7921  gctgtgaaag gtccgtgagc cgcatgactg cagagagtgc tgatactggc ctctctgcag
7981  atcatgt
```

FIG. 3D

```
   1    gccagccccc gattgggggc gacactccac catagatcac tccctgtga ggaactactg
  61    tcttcacgca gaaagcgtct agccatggcg ttagtatgag tgtcgtgcag cctccaggcc
 121    cccccctccc gggagagcca tagtggtctg cggaaccggt gagtacaccg gaattgccag
 181    gacgaccggg tcctttcttg gatcaacccg ctcaatgcct ggagatttgg gcgtgccccc
 241    gcgagactgc tagccgagta gtgttgggtc gcgaaaggcc ttgtggtact gcctgatagg
 301    gtgcttgcga gtgccccggg aggtctcgta gaccgtgcac catgagcacg aatcctaaac
 361    ctcaaagaaa aaccaagggg cgcgccatgc acccagaaac gctggtgaaa gtaaaagatg
 421    ctgaagatca gttgggtgca cgagtgggtt acatcgaact ggatctcaac agcggtaaga
 481    tccttgagag ttttcgcccc gaagaacgtt ttccaatgat gagcactttt aaagttctgc
 541    tatgtggcgc ggtattatcc cgtattgacg ccgggcaaga gcaactcggt cgccgcatac
 601    actattctca gaatgacttg gttgagtact caccagtcac agaaaagcat cttacggatg
 661    gcatgacagt aagagaatta tgcagtgctg ccataaccat gagtgataac actgcggcca
 721    acttacttct gacaacgatc ggaggaccga aggagctaac cgcttttttg cacaacatgg
 781    gggatcatgt aactcgcctt gatcgttggg aaccggagct gaatgaagcc ataccaaacg
 841    acgagcgtga caccacgatg cctgtagcaa tggcaacaac gttgcgcaaa ctattaactg
 901    gcgaactact tactctagct tcccggcaac aattaataga ctggatggag gcggataaag
 961    ttgcaggacc acttctgcgc tcggcccttc cggctggctg gtttattgct gataaatctg
1021    gagccggtga gcgtgggtct cgcggtatca ttgcagcact ggggccagat ggtaagccct
1081    cccgtatcgt agttatctac acgacgggga gtcaggcaac tatggatgaa cgaaatagac
1141    agatcgctga gataggtgcc tcactgatta gcattggta agtttaaaca gaccacaacg
1201    gtttcctct agcgggatca attccgcccc tctccctccc ccccctaa cgttactggc
1261    cgaagccgct tggaataagg ccggtgtgcg tttgtctata tgttatttc caccatattg
1321    ccgtcttttg gcaatgtgag ggcccggaaa cctggccctg tcttcttgac gagcattcct
1381    aggggtcttt cccctctcgc caaggaatg caaggtctgt tgaatgtcgt gaaggaagca
1441    gttcctctgg aagcttcttg aagacaaaca acgtctgtag cgaccctttg caggcagcgg
1501    aaccccccac ctggcgacag gtgcctctgc ggccaaaagc cacgtgtata agatacacct
1561    gcaaaggcgg cacaacccca gtgccacgtt gtgagttgga tagttgtgga aagagtcaaa
1621    tggctctcct caagcgtatt caacaagggg ctgaaggatg cccagaaggt acccattgt
1681    atgggatctg atctggggcc tcggtgcaca tgctttacat gtgtttagtc gaggttaaaa
1741    aaacgtctag gccccccgaa ccacggggac gtggttttcc tttgaaaaac acgataatac
1801    atggcgccta ttacggccta ctcccaacag acgcgaggcc tctagggtg tataatcacc
1861    agcctgactg gccgggacaa aaaccaagtg gagggtgagg tccagatcgt gtcaactgct
1921    acccaaacct tcctggcaac gtgcatcaat ggggtatgct ggactgtcta ccacggggcc
1981    ggaacgagga ccatcgcatc acccaagggt cctgtcatcc agatgtatac caatgtggac
```

FIG. 4A

```
2041  caagaccttg tgggctggcc cgctcctcaa ggttcccgct cattgacacc ctgcacctgc
2101  ggctcctcgg acctttacct ggttacgagg cacgccgacg tcattcccgt gcgccggcga
2161  ggtgatagca ggggtagcct gctttcgccc cggcccattt cctacctaaa aggctcctcg
2221  gggggtccgc tgttgtgccc cgcgggacac gccgtgggcc tattcagggc cgcggtgtgc
2281  acccgtggag tggccaaggc ggtggacttt atccctgtgg agaacctaga gacaaccatg
2341  agatccccgg tgttcacgga caactcctct ccaccagcag tgccccagag cttccaggtg
2401  gcccacctgc atgctcccac cggcagtggt aagagcacca aggtcccggc tgcgtacgca
2461  gcccagggct acaaggtgtt ggtgctcaac ccctctgttg ctgcaacgct gggctttggt
2521  gcttacatgt ccaaggccca tgggtcgat cctaatatca ggaccggggt gagaacaatt
2581  accactggca gccccatcac gtactccacc tacggcaagt tccttgccga cggcgggtgc
2641  tcaggaggcg cttatgacat aataatttgt gacgagtgcc actccacgga tgccacatcc
2701  atcttgggca tcggcactgt ccttgaccaa gcagagactg cgggggcgag attggttgtg
2761  ctcgccactg ctaccccctcc gggctccgtc actgtgtccc atcctaacat cgaggaggtt
2821  gctctgtcca ccaccggaga gatccctttc tacggcaagg ctatccccct cgaggtgatc
2881  aagggggggaa gacatctcat cttctgtcac tcaaagaaga agtgcgacga gctcgccgcg
2941  aagctggtcg cattgggcat caatgccgtg gcctactacc gcggacttga cgtgtctgtc
3001  atcccgacca gcggcgatgt tgtcgtcgtg tcaaccgatg ctctcatgac tggctttacc
3061  ggcgacttcg actctgtgat agactgcaac acgtgtgtca ctcagacagt cgatttcagc
3121  cttgacccta cctttaccat tgagacaacc acgctccccc aggatgctgt ctccaggact
3181  cagcgccggg gcaggactgg caggggaag ctaggcatct acagatttgt ggcaccgggg
3241  gagcgcccct ccggcatgtt cgactcgtcc gtcctctgtg agtgctatga cgcgggctgt
3301  gcttggtatg agctcacgcc cgccgagact accgttaggc tacgagcgta catgaacacc
3361  ccggggcttc ccgtgtgcca ggaccatctt gaatttttggg agggcgtctt tacgggcctc
3421  acccatatag atgcccactt tctatcccag acaaagcaga gtggggagaa ctttccttac
3481  ctggtagcgt accaagccac cgtgtgcgct agggctcaag cccctccccc atcgtgggac
3541  cagatgtgga agtgtttgat ccgccttaaa cccaccctcc atgggccaac acccctgcta
3601  tacagactgg gcgctgttca gaatgaagtc accctgacgc acccaatcac caaatacatc
3661  atgacatgca tgtcggccga cctggaggtc gtcacgagca cctgggtgct cgttggcggc
3721  gtcctggctg ctctggccgc gtattgcctg tcaacaggct gcgtggtcat agtgggcagg
3781  attgtcttgt ccgggaagcc ggcaattata cctgacaggg aggttctcta ccaggagttc
3841  gatgagatgg aagagtgctc tcagcactta ccgtacatcg agcaaggat gatgctcgct
3901  gagcagttca gcagaaggc cctcggcctc ctgcagaccg cgtcccgcca tgcagaggtt
3961  atcaccccctg ctgtccagac caactggcag aaactcgagg tcttctgggc gaagcacatg
4021  tggaatttca tcagtgggat acaatatttg gcgggcctgt caacgctgcc tggtaacccc
```

FIG. 4B

```
4081  gccattgctt cattgatggc ttttacagct gccgtcacca gcccactaac cactggccaa
4141  accctcctct tcaacatatt ggggggtgg gtggctgccc agctcgccgc cccggtgcc
4201  gctaccgcct ttgtgggcgc tggcttagct ggcgccgcca tcggcagcgt tggactgggg
4261  aaggtcctcg tggacattct tgcagggtat ggcgcgggcg tggcgggagc tcttgtagca
4321  ttcaagatca tgagcggtga ggtcccctcc acggaggacc tggtcaatct gctgcccgcc
4381  atcctctcgc ctggagccct tgtagtcggt gtggtctgcg cagcaatact gcgccggcac
4441  gttggcccgg gcgaggggggc agtgcaatgg atgaaccggc taatagcctt cgcctcccgg
4501  gggaaccatg tttcccccac gcactacgtg ccggagagcg atgcagccgc ccgcgtcact
4561  gccatactca gcagcctcac tgtaacccag ctcctgaggc gactacatca gtggataagc
4621  tcggagtgta ccactccatg ctccggctcc tggctaaggg acatctggga ctggatatgc
4681  gaggtgctga gcgactttaa gacctggctg aaagccaagc tcatgccaca actgcctggg
4741  attcccttg tgtcctgcca gcgcgggtat aggggggtct ggcgaggaga cggcattatg
4801  cacactcgct gccactgtgg agctgagatc actggacatg tcaaaaacgg gacgatgagg
4861  atcgtcggtc ctaggacctg caggaacatg tggagtggga cgttccccat taacgcctac
4921  accacgggcc cctgtactcc ccttcctgcg ccgaactata agttcgcgct gtggagggtg
4981  tctgcagagg aatacgtgga gataaggcgg gtgggggact tccactacgt atcgggtatg
5041  actactgaca atcttaaatg cccgtgccag atcccatcgc ccgaatttt cacagaattg
5101  gacggggtgc gcctacatag gtttgcgccc ccttgcaagc ccttgctgcg ggaggaggta
5161  tcattcagag taggactcca cgagtacccg gtggggtcgc aattaccttg cgagcccgaa
5221  ccggacgtag ccgtgttgac gtccatgctc actgatccct cccatataac agcagaggcg
5281  gccgggagaa ggttggcgag agggtcaccc ccttctatgg ccagctcctc ggccatccag
5341  ctgtccgctc catctctcaa ggcaacttgc accgccaacc atgactcccc tgacgccgag
5401  ctcatagagg ctaacctcct gtggaggcag gagatgggcg gcaacatcac cagggttgag
5461  tcagagaaca aagtggtgat tctggactcc ttcgatccgc ttgtggcaga ggaggatgag
5521  cgggaggtct ccgtacccgc agaaattctg cggaagtctc ggagattcgc ccgggccctg
5581  cccgtttggg cgcggccgga ctacaacccc ccgctagtag agacgtggaa aaagcctgac
5641  tacgaaccac ctgtggtcca tggctgcccg ctaccacctc cacggtcccc tcctgtgcct
5701  ccgcctcgga aaaagcgtac ggtggtcctc accgaatcaa ccctatctac tgccttggcc
5761  gagcttgcca ccaaaagttt tggcagctcc tcaacttccg gcattacggg cgacaatacg
5821  acaacatcct ctgagcccgc cccttctggc tgcccccccg actccgacgt tgagtcctat
5881  tcttccatgc ccccctgga gggggagcct ggggatccgg atctcagcga cgggtcatgg
5941  tcgacggtca gtagtggggc cgacacggaa gatgtcgtgt gctgctcaat gtcttattcc
6001  tggacaggcg cactcgtcac ccgtgcgct gcggaagaac aaaaactgcc catcaacgca
6061  ctgagcaact cgttgctacg ccatcacaat ctggtatatt ccaccacttc acgcagtgct
```

FIG. 4C

```
6121  tgccaaaggc agaagaaagt cacatttgac agactgcaag ttctggacag ccattaccag
6181  gacgtgctca aggaggtcaa agcagcggcg tcaaaagtga aggctaactt gctatccgta
6241  gaggaagctt gcagcctgac gcccccacat tcagccaaat ccaagtttgg ctatggggca
6301  aaagacgtcc gttgccatgc cagaaaggcc gtagcccaca tcaactccgt gtggaaagac
6361  cttctggaag acagtgtaac accaatagac actaccatca tggccaagaa cgaggtcttc
6421  tgcgttcagc ctgagaaggg gggtcgtaag ccagctcgtc tcatcgtgtt ccccgacctg
6481  ggcgtgcgcg tgtgcgagaa gatggccctg tacgacgtgg ttagcaaact cccctggcc
6541  gtgatgggaa gctcctacgg attccaatac tcaccaggac agcgggttga attcctcgtg
6601  caagcgtgga agtccaagaa gaccccgatg gggttctcgt atgatacccg ctgttttgac
6661  tccacagtca ctgagagcga catccgtacg gaggaggcaa tttaccaatg ttgtgacctg
6721  gaccccaag cccgcgtggc catcaagtcc ctcactgaga ggctttatgt tgggggccct
6781  cttaccaatt caaggggga aaactgcggc tatcgcaggt gccgcgcgag cggcgtactg
6841  acaactagct gtggtaacac cctcacttgc tacatcaagg cccgggcagc ctgtcgagcc
6901  gcaggctcc aggactgcac catgctcgtg tgtggcgacg acttagtcgt tatctgtgaa
6961  agtgcggggg tccaggagga cgcggcgagc ctgagagcct tacggaggc tatgaccagg
7021  tactccgccc cccccgggga cccccacaa ccagaatacg acttggagct tataacatca
7081  tgctcctcca acgtgtcagt cgcccacgac ggcgctggaa aagggtcta ctaccttacc
7141  cgtgaccta caacccccct cgcgagagcc gcgtgggaga cagcaagaca cactccagtc
7201  aattcctggc taggcaacat aatcatgttt gcccccacac tgtgggcgag gatgatactg
7261  atgacccatt tctttagcgt cctcatagcc agggatcagc ttgaacaggc tcttaactgt
7321  gagatctacg gagcctgcta ctccatagaa ccactggatc tacctccaat cattcaaaga
7381  ctccatggcc tcagcgcatt tcactccac agttactctc caggtgaaat caataggggtg
7441  gccgcatgcc tcagaaaact tggggtcccg cccttgcgag cttggagaca ccgggcccgg
7501  agcgtccgcg ctaggcttct gtccagggga ggcagggctg ccatatgtgg caagtacctc
7561  ttcaactggg cagtaagaac aaagctcaaa ctcactccaa tagcggccgc tggccggctg
7621  gacttgtccg gttggttcac ggctggctac agcgggggag acatttatca cagcgtgtct
7681  catgcccggc ccgctggtt ctggttttgc ctactcctgc tcgctgcagg ggtaggcatc
7741  tacctcctcc caaatcgatg aaggttgggg taaacactcc ggcctcttag gccatttcgt
7801  gtcttttttt tgttttttt tttgttttt tcttttttt ttttttttt ttcttttttc
7861  cttcttcctt ttctcttttt ttcttcttta atggtggctc catcttagcc ctagtcacgg
7921  ctagctgtga aaggtccgtg agccgcatga ctgcagagag tgctgatact ggcctctctg
7981  cagatcatgt
```

FIG. 4D

SEQUENCE LISTING

<160> NUMBER OF SEQ ID NOS: 4

<210> SEQ ID NO 1
<211> LENGTH: 1985
<212> TYPE: PRT
<213> ORGANISM: Artificial Sequence
<220> FEATURE:
<223> OTHER INFORMATION: HCV Replicon

<400> SEQUENCE: 1

```
Met Ala Pro Ile Thr Ala Tyr Ser Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Val Val Ser Thr Ala Thr Gln Ser Phe Leu Ala Thr Cys
        35                  40                  45

Val Asn Gly Val Cys Trp Thr Val Tyr His Gly Ala Gly Ser Lys Thr
    50                  55                  60

Leu Ala Gly Pro Lys Gly Pro Ile Thr Gln Met Tyr Thr Asn Val Asp
65                  70                  75                  80

Gln Asp Leu Val Gly Trp Gln Ala Pro Pro Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Val Ser Tyr Leu Lys Gly Ser Ser Gly Gly Pro Leu
    130                 135                 140

Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
                165                 170                 175

Glu Thr Thr Met Arg Ser Pro Val Phe Thr Asp Asn Ser Ser Pro Pro
            180                 185                 190

Ala Val Pro Gln Ser Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ala Pro Val Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ser Thr Thr Ile Leu Gly Ile
    290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Asn Thr Gly Glu Ile Pro Phe Tyr Gly
            340                 345                 350
```

```
Lys Ala Ile Pro Ile Glu Ala Ile Arg Gly Gly Arg His Leu Ile Phe
            355                 360                 365

Cys His Ser Lys Lys Cys Asp Glu Leu Ala Ala Lys Leu Ser Gly
        370                 375                 380

Leu Gly Ile Asn Ala Val Ala Tyr Tyr Arg Gly Leu Asp Val Ser Val
385                 390                 395                 400

Ile Pro Thr Ile Gly Asp Val Val Val Ala Thr Asp Ala Leu Met
            405                 410                 415

Thr Gly Tyr Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Thr Thr Val Pro Gln Asp Ala Val Ser Arg Ser Gln Arg Gly
    450                 455                 460

Arg Thr Gly Arg Gly Arg Met Gly Ile Tyr Arg Phe Val Thr Pro Gly
465                 470                 475                 480

Glu Arg Pro Ser Gly Met Phe Asp Ser Val Leu Cys Glu Cys Tyr
            485                 490                 495

Asp Ala Gly Cys Ala Trp Tyr Glu Leu Thr Pro Ala Glu Thr Ser Val
            500                 505                 510

Arg Leu Arg Ala Tyr Leu Asn Thr Pro Gly Leu Pro Val Cys Gln Asp
        515                 520                 525

His Leu Glu Phe Trp Glu Ser Val Phe Thr Gly Leu Thr His Ile Asp
        530                 535                 540

Ala His Phe Leu Ser Gln Thr Lys Gln Ala Gly Asp Asn Phe Pro Tyr
545                 550                 555                 560

Leu Val Ala Tyr Gln Ala Thr Val Cys Ala Arg Ala Gln Ala Pro Pro
            565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Ile Thr Lys Tyr Ile Met Ala Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Thr Thr Gly Ser Val Val
            645                 650                 655

Ile Val Gly Arg Ile Ile Leu Ser Gly Arg Pro Ala Ile Val Pro Asp
            660                 665                 670

Arg Glu Phe Leu Tyr Gln Glu Phe Asp Glu Met Glu Glu Cys Ala Ser
        675                 680                 685

His Leu Pro Tyr Ile Glu Gln Gly Met Gln Leu Ala Glu Gln Phe Lys
        690                 695                 700

Gln Lys Ala Leu Gly Leu Leu Gln Thr Ala Thr Lys Gln Ala Glu Ala
705                 710                 715                 720

Ala Ala Pro Val Val Glu Ser Lys Trp Arg Ala Leu Glu Thr Phe Trp
            725                 730                 735

Ala Lys His Met Trp Asn Phe Ile Ser Gly Ile Gln Tyr Leu Ala Gly
            740                 745                 750

Leu Ser Thr Leu Pro Gly Asn Pro Ala Ile Ala Ser Leu Met Ala Phe
        755                 760                 765
```

-continued

```
Thr Ala Ser Ile Thr Ser Pro Leu Thr Thr Gln Ser Thr Leu Leu Phe
    770             775                 780

Asn Ile Leu Gly Gly Trp Val Ala Ala Gln Leu Ala Pro Pro Ser Ala
785             790                 795                 800

Ala Ser Ala Phe Val Gly Ala Gly Ile Ala Gly Ala Ala Val Gly Ser
            805                 810                 815

Ile Gly Leu Gly Lys Val Leu Val Asp Ile Leu Ala Gly Tyr Gly Ala
                820                 825                 830

Gly Val Ala Gly Ala Leu Val Ala Phe Lys Val Met Ser Gly Glu Met
                835                 840                 845

Pro Ser Thr Glu Asp Leu Val Asn Leu Leu Pro Ala Ile Leu Ser Pro
    850                 855                 860

Gly Ala Leu Val Val Gly Val Val Cys Ala Ala Ile Leu Arg Arg His
865             870                 875                 880

Val Gly Pro Gly Glu Gly Ala Val Gln Trp Met Asn Arg Leu Ile Ala
                885                 890                 895

Phe Ala Ser Arg Gly Asn His Val Ser Pro Thr His Tyr Val Pro Glu
            900                 905                 910

Ser Asp Ala Ala Ala Arg Val Thr Gln Ile Leu Ser Ser Leu Thr Ile
            915                 920                 925

Thr Gln Leu Leu Lys Arg Leu His Gln Trp Ile Asn Glu Asp Cys Ser
    930                 935                 940

Thr Pro Cys Ser Gly Ser Trp Leu Arg Asp Val Trp Asp Trp Ile Cys
945             950                 955                 960

Thr Val Leu Thr Asp Phe Lys Thr Trp Leu Gln Ser Lys Leu Leu Pro
                965                 970                 975

Gln Leu Pro Gly Val Pro Phe Phe Ser Cys Gln Arg Gly Tyr Lys Gly
            980                 985                 990

Val Trp Arg Gly Asp Gly Ile Met Gln Thr Thr Cys Pro Cys Gly Ala
            995                 1000                1005

Gln Ile Thr Gly His Val Lys Asn Gly Ser Met Arg Ile Val Gly Pro
    1010                1015                1020

Lys Thr Cys Ser Asn Thr Trp His Gly Thr Phe Pro Ile Asn Ala Tyr
1025                1030                1035                1040

Thr Thr Gly Pro Cys Thr Pro Ser Pro Ala Pro Asn Tyr Ser Arg Ala
                1045                1050                1055

Leu Trp Arg Val Ala Ala Glu Glu Tyr Val Glu Val Thr Arg Val Gly
                1060                1065                1070

Asp Phe His Tyr Val Thr Gly Met Thr Thr Asp Asn Val Lys Cys Pro
    1075                1080                1085

Cys Gln Val Pro Ala Pro Glu Phe Phe Thr Glu Val Asp Gly Val Arg
    1090                1095                1100

Leu His Arg Tyr Ala Pro Ala Cys Arg Pro Leu Leu Arg Glu Glu Val
1105                1110                1115                1120

Thr Phe Gln Val Gly Leu Asn Gln Tyr Leu Val Gly Ser Gln Leu Pro
                1125                1130                1135

Cys Glu Pro Glu Pro Asp Val Ala Val Leu Thr Ser Met Leu Thr Asp
            1140                1145                1150

Pro Ser His Ile Thr Ala Glu Thr Ala Lys Arg Arg Leu Ala Arg Gly
            1155                1160                1165

Ser Pro Pro Ser Leu Ala Ser Ser Ser Ala Ile Gln Leu Ser Ala Pro
    1170                1175                1180

Ser Leu Lys Ala Thr Cys Thr Thr His His Val Ser Pro Asp Ala Asp
```

-continued

```
            1185                1190                1195                1200
Leu Ile Glu Ala Asn Leu Leu Trp Arg Gln Glu Met Gly Gly Asn Ile
                1205                1210                1215
Thr Arg Val Glu Ser Glu Asn Lys Val Val Leu Asp Ser Phe Asp
    1220                1225                1230
Pro Leu Arg Ala Glu Glu Asp Glu Arg Glu Val Ser Val Pro Ala Glu
        1235                1240                1245
Ile Leu Arg Lys Ser Lys Lys Phe Pro Ala Ala Met Pro Ile Trp Ala
        1250                1255                1260
Arg Pro Asp Tyr Asn Pro Pro Leu Leu Glu Ser Trp Lys Asp Pro Asp
1265                1270                1275                1280
Tyr Val Pro Pro Val Val His Gly Cys Pro Leu Pro Pro Ile Lys Ala
                1285                1290                1295
Pro Pro Ile Pro Pro Arg Arg Lys Arg Thr Val Val Leu Thr Glu
        1300                1305                1310
Ser Ser Val Ser Ser Ala Leu Ala Glu Leu Ala Thr Lys Thr Phe Gly
        1315                1320                1325
Ser Ser Glu Ser Ser Ala Val Asp Ser Gly Thr Ala Thr Ala Leu Pro
        1330                1335                1340
Asp Gln Ala Ser Asp Asp Gly Asp Lys Gly Ser Asp Val Glu Ser Tyr
1345                1350                1355                1360
Ser Ser Met Pro Pro Leu Glu Gly Glu Pro Gly Asp Pro Asp Leu Ser
                1365                1370                1375
Asp Gly Ser Trp Ser Thr Val Ser Glu Glu Ala Ser Glu Asp Val Val
        1380                1385                1390
Cys Cys Ser Met Ser Tyr Thr Trp Thr Gly Ala Leu Ile Thr Pro Cys
        1395                1400                1405
Ala Ala Glu Glu Ser Lys Leu Pro Ile Asn Ala Leu Ser Asn Ser Leu
        1410                1415                1420
Leu Arg His His Asn Met Val Tyr Ala Thr Thr Ser Arg Ser Ala Gly
1425                1430                1435                1440
Leu Arg Gln Lys Lys Val Thr Phe Asp Arg Leu Gln Val Leu Asp Asp
                1445                1450                1455
His Tyr Arg Asp Val Leu Lys Glu Met Lys Ala Lys Ala Ser Thr Val
            1460                1465                1470
Lys Ala Lys Leu Leu Ser Val Glu Glu Ala Cys Lys Leu Thr Pro Pro
        1475                1480                1485
His Ser Ala Lys Ser Lys Phe Gly Tyr Gly Ala Lys Asp Val Arg Asn
        1490                1495                1500
Leu Ser Ser Lys Ala Val Asn His Ile His Ser Val Trp Lys Asp Leu
1505                1510                1515                1520
Leu Glu Asp Thr Val Thr Pro Ile Asp Thr Thr Ile Met Ala Lys Asn
                1525                1530                1535
Glu Val Phe Cys Val Gln Pro Glu Lys Gly Gly Arg Lys Pro Ala Arg
            1540                1545                1550
Leu Ile Val Phe Pro Asp Leu Gly Val Arg Val Cys Glu Lys Met Ala
        1555                1560                1565
Leu Tyr Asp Val Val Ser Thr Leu Pro Gln Val Met Gly Ser Ser
        1570                1575                1580
Tyr Gly Phe Gln Tyr Ser Pro Gly Gln Arg Val Glu Phe Leu Val Asn
1585                1590                1595                1600
Thr Trp Lys Ser Lys Lys Asn Pro Met Gly Phe Ser Tyr Asp Thr Arg
                1605                1610                1615
```

Cys Phe Asp Ser Thr Val Thr Glu Asn Asp Ile Arg Val Glu Glu Ser
            1620                1625                1630

Ile Tyr Gln Cys Cys Asp Leu Ala Pro Glu Ala Arg Gln Ala Ile Lys
        1635                1640                1645

Ser Leu Thr Glu Arg Leu Tyr Ile Gly Gly Pro Leu Thr Asn Ser Lys
    1650                1655                1660

Gly Gln Asn Cys Gly Tyr Arg Arg Cys Arg Ala Ser Gly Val Leu Thr
1665                1670                1675                1680

Thr Ser Cys Gly Asn Thr Leu Thr Cys Tyr Leu Lys Ala Ser Ala Ala
            1685                1690                1695

Cys Arg Ala Ala Lys Leu Gln Asp Cys Thr Met Leu Val Asn Gly Asp
        1700                1705                1710

Asp Leu Val Val Ile Cys Glu Ser Ala Gly Thr Gln Glu Asp Ala Ala
    1715                1720                1725

Ser Leu Arg Val Phe Thr Glu Ala Met Thr Arg Tyr Ser Ala Pro Pro
1730                1735                1740

Gly Asp Pro Pro Gln Pro Glu Tyr Asp Leu Glu Leu Ile Thr Ser Cys
1745                1750                1755                1760

Ser Ser Asn Val Ser Val Ala His Asp Ala Ser Gly Lys Arg Val Tyr
            1765                1770                1775

Tyr Leu Thr Arg Asp Pro Thr Thr Pro Leu Ala Arg Ala Ala Trp Glu
        1780                1785                1790

Thr Ala Arg His Thr Pro Val Asn Ser Trp Leu Gly Asn Ile Ile Met
    1795                1800                1805

Tyr Ala Pro Thr Leu Trp Ala Arg Met Ile Leu Met Thr His Phe Phe
1810                1815                1820

Ser Ile Leu Leu Ala Gln Glu Gln Leu Glu Lys Ala Leu Asp Cys Gln
1825                1830                1835                1840

Ile Tyr Gly Ala Cys Tyr Ser Ile Glu Pro Leu Asp Leu Pro Gln Ile
            1845                1850                1855

Ile Glu Arg Leu His Gly Leu Ser Ala Phe Ser Leu His Ser Tyr Ser
        1860                1865                1870

Pro Gly Glu Ile Asn Arg Val Ala Ser Cys Leu Arg Lys Leu Gly Val
    1875                1880                1885

Pro Pro Leu Arg Ala Trp Arg His Arg Ala Arg Asn Val Arg Ala Arg
1890                1895                1900

Leu Leu Ser Arg Gly Gly Arg Ala Ala Ile Cys Gly Lys Tyr Leu Phe
1905                1910                1915                1920

Asn Trp Ala Val Arg Thr Lys Leu Lys Leu Thr Pro Ile Ala Ala Ala
            1925                1930                1935

Gly Arg Leu Asp Leu Ser Ser Trp Phe Thr Ala Gly Tyr Ser Gly Gly
        1940                1945                1950

Asp Ile Tyr His Gly Val Ser His Ala Arg Pro Arg Trp Phe Trp Phe
    1955                1960                1965

Cys Leu Leu Leu Leu Ala Ala Gly Ile Gly Ile Tyr Leu Leu Pro Asn
1970                1975                1980

Arg
1985

<210> SEQ ID NO 2
<211> LENGTH: 1986
<212> TYPE: PRT
<213> ORGANISM: Artificial Sequence
<220> FEATURE:

<223> OTHER INFORMATION: HCV Replicon

<400> SEQUENCE: 2

```
Met Ala Pro Ile Thr Ala Tyr Ala Gln Gln Thr Arg Gly Leu Leu Gly
  1               5                  10                  15

Cys Ile Ile Thr Ser Leu Thr Gly Arg Asp Lys Asn Gln Val Glu Gly
             20                  25                  30

Glu Val Gln Ile Val Ser Thr Ala Thr Gln Thr Phe Leu Ala Thr Cys
         35                  40                  45

Ile Asn Gly Val Cys Trp Thr Val Tyr His Gly Ala Gly Thr Arg Thr
 50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ser Arg Ser Leu Thr
             85                  90                  95

Pro Cys Thr Cys Gly Ser Ser Asp Leu Tyr Leu Val Thr Arg His Ala
        100                 105                 110

Asp Val Ile Pro Val Arg Arg Arg Gly Asp Ser Arg Gly Ser Leu Leu
        115                 120                 125

Ser Pro Arg Pro Ile Ser Tyr Leu Lys Gly Ser Ser Gly Gly Pro Leu
        130                 135                 140

Leu Cys Pro Ala Gly His Ala Val Gly Leu Phe Arg Ala Ala Val Cys
145                 150                 155                 160

Thr Arg Gly Val Ala Lys Ala Val Asp Phe Ile Pro Val Glu Asn Leu
                165                 170                 175

Glu Thr Thr Met Arg Ser Pro Val Phe Thr Asp Asn Ser Ser Pro Pro
                180                 185                 190

Ala Val Pro Gln Ser Phe Gln Val Ala His Leu His Ala Pro Thr Gly
            195                 200                 205

Ser Gly Lys Ser Thr Lys Val Pro Ala Ala Tyr Ala Ala Gln Gly Tyr
        210                 215                 220

Lys Val Leu Val Leu Asn Pro Ser Val Ala Ala Thr Leu Gly Phe Gly
225                 230                 235                 240

Ala Tyr Met Ser Lys Ala His Gly Val Asp Pro Asn Ile Arg Thr Gly
                245                 250                 255

Val Arg Thr Ile Thr Thr Gly Ser Pro Ile Thr Tyr Ser Thr Tyr Gly
                260                 265                 270

Lys Phe Leu Ala Asp Gly Gly Cys Ser Gly Gly Ala Tyr Asp Ile Ile
            275                 280                 285

Ile Cys Asp Glu Cys His Ser Thr Asp Ala Thr Ser Ile Leu Gly Ile
        290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Ser His Pro Asn
                325                 330                 335

Ile Glu Glu Val Ala Leu Ser Thr Thr Gly Glu Ile Pro Phe Tyr Gly
                340                 345                 350

Lys Ala Ile Pro Leu Glu Val Ile Lys Gly Gly Arg His Leu Ile Phe
            355                 360                 365

Cys His Ser Lys Lys Cys Asp Glu Leu Ala Ala Lys Leu Val Ala
        370                 375                 380

Leu Gly Ile Asn Ala Val Ala Tyr Tyr Arg Gly Leu Asp Val Ser Val
385                 390                 395                 400
```

-continued

```
Ile Pro Thr Ser Gly Asp Val Val Val Ser Thr Asp Ala Leu Met
            405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
            435                 440                 445

Thr Thr Thr Leu Pro Gln Asp Ala Val Ser Arg Thr Gln Arg Arg Gly
450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                    485                 490                 495

Asp Ala Gly Cys Ala Trp Tyr Glu Leu Thr Pro Ala Glu Thr Thr Val
                500                 505                 510

Arg Leu Arg Ala Tyr Met Asn Thr Pro Gly Leu Pro Val Cys Gln Asp
            515                 520                 525

His Leu Glu Phe Trp Glu Gly Val Phe Thr Gly Leu Thr His Ile Asp
            530                 535                 540

Ala His Phe Leu Ser Gln Thr Lys Gln Ser Gly Glu Asn Phe Pro Tyr
545                 550                 555                 560

Leu Val Ala Tyr Gln Ala Thr Val Cys Ala Arg Ala Gln Ala Pro Pro
                    565                 570                 575

Pro Ser Trp Asp Gln Met Trp Lys Cys Leu Ile Arg Leu Lys Pro Thr
                580                 585                 590

Leu His Gly Pro Thr Pro Leu Leu Tyr Arg Leu Gly Ala Val Gln Asn
            595                 600                 605

Glu Val Thr Leu Thr His Pro Ile Thr Lys Tyr Ile Met Thr Cys Met
610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                    645                 650                 655

Ile Val Gly Arg Ile Val Leu Ser Gly Lys Pro Ala Ile Ile Pro Asp
                660                 665                 670

Arg Glu Val Leu Tyr Gln Glu Phe Asp Glu Met Glu Glu Cys Ser Gln
            675                 680                 685

His Leu Pro Tyr Ile Glu Gln Gly Met Met Leu Ala Glu Gln Phe Lys
            690                 695                 700

Gln Lys Ala Leu Gly Leu Leu Gln Thr Ala Ser Arg His Ala Glu Val
705                 710                 715                 720

Ile Thr Pro Ala Val Gln Thr Asn Trp Gln Lys Leu Glu Val Phe Trp
                    725                 730                 735

Ala Lys His Met Trp Asn Phe Ile Ser Gly Ile Gln Tyr Leu Ala Gly
                740                 745                 750

Leu Ser Thr Leu Pro Gly Asn Pro Ala Ile Ala Ser Leu Met Ala Phe
            755                 760                 765

Thr Ala Ala Val Thr Ser Pro Leu Thr Thr Gly Gln Thr Leu Leu Phe
            770                 775                 780

Asn Ile Leu Gly Gly Trp Val Ala Ala Gln Leu Ala Ala Pro Gly Ala
785                 790                 795                 800

Ala Thr Ala Phe Val Gly Ala Gly Leu Ala Gly Ala Ala Ile Gly Ser
                    805                 810                 815

Val Gly Leu Gly Lys Val Leu Val Asp Ile Leu Ala Gly Tyr Gly Ala
```

-continued

|     |     |     | 820 |     |     |     | 825 |     |     |     | 830 |     |     |
|-----|-----|-----|-----|-----|-----|-----|-----|-----|-----|-----|-----|-----|-----|

Gly Val Ala Gly Ala Leu Val Ala Phe Lys Ile Met Ser Gly Glu Val
            835                 840                 845

Pro Ser Thr Glu Asp Leu Val Asn Leu Leu Pro Ala Ile Leu Ser Pro
        850                 855                 860

Gly Ala Leu Val Val Gly Val Val Cys Ala Ala Ile Leu Arg Arg His
865                 870                 875                 880

Val Gly Pro Gly Glu Gly Ala Val Gln Trp Met Asn Arg Leu Ile Ala
                885                 890                 895

Phe Ala Ser Arg Gly Asn His Val Ser Pro Thr His Tyr Val Pro Glu
            900                 905                 910

Ser Asp Ala Ala Ala Arg Val Thr Ala Ile Leu Ser Ser Leu Thr Val
        915                 920                 925

Thr Gln Leu Leu Arg Arg Leu His Gln Trp Ile Ser Ser Glu Cys Thr
    930                 935                 940

Thr Pro Cys Ser Gly Ser Trp Leu Arg Asp Ile Trp Asp Trp Ile Cys
945                 950                 955                 960

Glu Val Leu Ser Asp Phe Lys Thr Trp Leu Lys Ala Lys Leu Met Pro
                965                 970                 975

Gln Leu Pro Gly Ile Pro Phe Val Ser Cys Gln Arg Gly Tyr Arg Gly
            980                 985                 990

Val Trp Arg Gly Asp Gly Ile Met His Thr Arg Cys His Cys Gly Ala
        995                 1000                1005

Glu Ile Thr Gly His Val Lys Asn Gly Thr Met Arg Ile Val Gly Pro
    1010                1015                1020

Arg Thr Cys Arg Asn Met Trp Ser Gly Thr Phe Pro Ile Asn Ala Tyr
1025                1030                1035                1040

Thr Thr Gly Pro Cys Thr Pro Leu Pro Ala Pro Asn Tyr Lys Phe Ala
                1045                1050                1055

Leu Trp Arg Val Ser Ala Glu Glu Tyr Val Glu Ile Arg Arg Val Gly
            1060                1065                1070

Asp Phe His Tyr Val Ser Gly Met Thr Thr Asp Asn Leu Lys Cys Pro
        1075                1080                1085

Cys Gln Ile Pro Ser Pro Glu Phe Phe Thr Glu Leu Asp Gly Val Arg
    1090                1095                1100

Leu His Arg Phe Ala Pro Pro Cys Lys Pro Leu Leu Arg Glu Glu Val
1105                1110                1115                1120

Ser Phe Arg Val Gly Leu His Glu Tyr Pro Val Gly Ser Gln Leu Pro
                1125                1130                1135

Cys Glu Pro Glu Pro Asp Val Ala Val Leu Thr Ser Met Leu Thr Asp
            1140                1145                1150

Pro Ser His Ile Thr Ala Glu Ala Ala Gly Arg Arg Leu Ala Arg Gly
        1155                1160                1165

Ser Pro Pro Ser Met Ala Ser Ser Ser Ala Ile Gln Leu Ser Ala Pro
    1170                1175                1180

Ser Leu Lys Ala Thr Cys Thr Ala Asn His Asp Ser Pro Asp Ala Glu
1185                1190                1195                1200

Leu Ile Glu Ala Asn Leu Leu Trp Arg Gln Glu Met Gly Gly Asn Ile
                1205                1210                1215

Thr Arg Val Glu Ser Glu Asn Lys Val Val Ile Leu Asp Ser Phe Asp
            1220                1225                1230

Pro Leu Val Ala Glu Glu Asp Glu Arg Glu Val Ser Val Pro Ala Glu
        1235                1240                1245

```
Ile Leu Arg Lys Ser Arg Arg Phe Ala Arg Ala Leu Pro Val Trp Ala
    1250                1255                1260

Arg Pro Asp Tyr Asn Pro Pro Leu Val Glu Thr Trp Lys Lys Pro Asp
1265            1270                1275                1280

Tyr Glu Pro Pro Val Val His Gly Cys Pro Leu Pro Pro Arg Ser
        1285                1290                1295

Pro Pro Val Pro Pro Arg Lys Lys Arg Thr Val Val Leu Thr Glu
    1300                1305                1310

Ser Thr Leu Ser Thr Ala Leu Ala Glu Leu Ala Thr Lys Ser Phe Gly
    1315                1320                1325

Ser Ser Ser Thr Ser Gly Ile Thr Gly Asp Asn Thr Thr Ser Ser
    1330                1335                1340

Glu Pro Ala Pro Ser Gly Cys Pro Asp Ser Asp Val Glu Ser Tyr
1345            1350                1355                1360

Ser Ser Met Pro Pro Leu Glu Gly Glu Pro Gly Asp Pro Asp Leu Ser
            1365                1370                1375

Asp Gly Ser Trp Ser Thr Val Ser Ser Gly Ala Asp Thr Glu Asp Val
            1380                1385                1390

Val Cys Cys Ser Met Ser Tyr Ser Trp Thr Gly Ala Leu Val Thr Pro
    1395                1400                1405

Cys Ala Glu Glu Gln Lys Leu Pro Ile Asn Ala Leu Ser Asn Ser
    1410                1415                1420

Leu Leu Arg His His Asn Leu Val Tyr Ser Thr Thr Ser Arg Ser Ala
1425            1430                1435                1440

Cys Gln Arg Gln Lys Lys Val Thr Phe Asp Arg Leu Gln Val Leu Asp
            1445                1450                1455

Ser His Tyr Gln Asp Val Leu Lys Glu Val Lys Ala Ala Ser Lys
        1460                1465                1470

Val Lys Ala Asn Leu Leu Ser Val Glu Glu Ala Cys Ser Leu Thr Pro
            1475                1480                1485

Pro His Ser Ala Lys Ser Lys Phe Gly Tyr Gly Ala Lys Asp Val Arg
    1490                1495                1500

Cys His Ala Arg Lys Ala Val Ala His Ile Asn Ser Val Trp Lys Asp
1505            1510                1515                1520

Leu Leu Glu Asp Ser Val Thr Pro Ile Asp Thr Thr Ile Met Ala Lys
            1525                1530                1535

Asn Glu Val Phe Cys Val Gln Pro Glu Lys Gly Gly Arg Lys Pro Ala
            1540                1545                1550

Arg Leu Ile Val Phe Pro Asp Leu Gly Val Arg Val Cys Glu Lys Met
    1555                1560                1565

Ala Leu Tyr Asp Val Val Ser Lys Leu Pro Leu Ala Val Met Gly Ser
    1570                1575                1580

Ser Tyr Gly Phe Gln Tyr Ser Pro Gly Gln Arg Val Glu Phe Leu Val
1585            1590                1595                1600

Gln Ala Trp Lys Ser Lys Lys Thr Pro Met Gly Phe Ser Tyr Asp Thr
            1605                1610                1615

Arg Cys Phe Asp Ser Thr Val Thr Glu Ser Asp Ile Arg Thr Glu Glu
            1620                1625                1630

Ala Ile Tyr Gln Cys Cys Asp Leu Asp Pro Gln Ala Arg Val Ala Ile
            1635                1640                1645

Lys Ser Leu Thr Glu Arg Leu Tyr Val Gly Gly Pro Leu Thr Asn Ser
    1650                1655                1660
```

-continued

Arg Gly Glu Asn Cys Gly Tyr Arg Arg Cys Arg Ala Ser Gly Val Leu
1665                1670                1675                1680

Thr Thr Ser Cys Gly Asn Thr Leu Thr Cys Tyr Ile Lys Ala Arg Ala
            1685                1690                1695

Ala Cys Arg Ala Ala Gly Leu Gln Asp Cys Thr Met Leu Val Cys Gly
        1700                1705                1710

Asp Asp Leu Val Val Ile Cys Glu Ser Ala Gly Val Gln Glu Asp Ala
    1715                1720                1725

Ala Ser Leu Arg Ala Phe Thr Glu Ala Met Thr Arg Tyr Ser Ala Pro
1730                1735                1740

Pro Gly Asp Pro Pro Gln Pro Glu Tyr Asp Leu Glu Leu Ile Thr Ser
1745                1750                1755                1760

Cys Ser Ser Asn Val Ser Val Ala His Asp Gly Ala Gly Lys Arg Val
            1765                1770                1775

Tyr Tyr Leu Thr Arg Asp Pro Thr Thr Pro Leu Ala Arg Ala Ala Trp
        1780                1785                1790

Glu Thr Ala Arg His Thr Pro Val Asn Ser Trp Leu Gly Asn Ile Ile
    1795                1800                1805

Met Phe Ala Pro Thr Leu Trp Ala Arg Met Ile Leu Met Thr His Phe
    1810                1815                1820

Phe Ser Val Leu Ile Ala Arg Asp Gln Leu Glu Gln Ala Leu Asn Cys
1825                1830                1835                1840

Glu Ile Tyr Gly Ala Cys Tyr Ser Ile Glu Pro Leu Asp Leu Pro Pro
            1845                1850                1855

Ile Ile Gln Arg Leu His Gly Leu Ser Ala Phe Ser Leu His Ser Tyr
        1860                1865                1870

Ser Pro Gly Glu Ile Asn Arg Val Ala Ala Cys Leu Arg Lys Leu Gly
    1875                1880                1885

Val Pro Pro Leu Arg Ala Trp Arg His Arg Ala Arg Ser Val Arg Ala
1890                1895                1900

Arg Leu Leu Ser Arg Gly Gly Arg Ala Ala Ile Cys Gly Lys Tyr Leu
1905                1910                1915                1920

Phe Asn Trp Ala Val Arg Thr Lys Leu Lys Leu Thr Pro Ile Ala Ala
            1925                1930                1935

Ala Gly Arg Leu Asp Leu Ser Gly Trp Phe Thr Ala Gly Tyr Ser Gly
        1940                1945                1950

Gly Asp Ile Tyr His Ser Val Ser His Ala Arg Pro Arg Trp Phe Trp
    1955                1960                1965

Phe Cys Leu Leu Leu Leu Ala Ala Gly Val Gly Ile Tyr Leu Leu Pro
    1970                1975                1980

Asn Arg
1985

<210> SEQ ID NO 3
<211> LENGTH: 7987
<212> TYPE: DNA
<213> ORGANISM: Artificial Sequence
<220> FEATURE:
<223> OTHER INFORMATION: Chimeric HCV Replicon

<400> SEQUENCE: 3 gccagcccccc gattgggggc gacactccac catagatcac tcccctgtga ggaactactg    60
tcttcacgca gaaagcgtct agccatggcg ttagtatgag tgtcgtgcag cctccaggcc    120 ccccctccc gggagagcca tagtggtctg cggaaccggt gagtacaccg gaattgccag    180

```
gacgaccggg tcctttcttg gatcaacccg ctcaatgcct ggagatttgg gcgtgccccc      240
gcgagactgc tagccgagta gtgttgggtc gcgaaaggcc ttgtggtact gcctgatagg      300
gtgcttgcga gtgccccggg aggtctcgta gaccgtgcac catgagcacg aatcctaaac      360
ctcaaagaaa aaccaaaggg cgcgccatgc acccagaaac gctggtgaaa gtaaaagatg      420
ctgaagatca gttgggtgca cgagtgggtt acatcgaact ggatctcaac agcggtaaga      480
tccttgagag ttttcgcccc gaagaacgtt ttccaatgat gagcactttt aaagttctgc      540
tatgtggcgc ggtattatcc cgtattgacg ccgggcaaga gcaactcggt cgccgcatac      600
actattctca gaatgacttg gttgagtact caccagtcac agaaaagcat cttacggatg      660
gcatgacagt aagagaatta tgcagtgctg ccataaccat gagtgataac actgcggcca      720
acttacttct gacaacgatc ggaggaccga aggagctaac cgcttttttg cacaacatgg      780
gggatcatgt aactcgcctt gatcgttggg aaccggagct gaatgaagcc ataccaaacg      840
acgagcgtga caccacgatg cctgtagcaa tggcaacaac gttgcgcaaa ctattaactg      900
gcgaactact tactctagct tcccggcaac aattaataga ctggatggag gcggataaag      960
ttgcaggacc acttctgcgc tcggcccttc cggctggctg gtttattgct gataaatctg     1020
gagccggtga gcgtgggtct cgcggtatca ttgcagcact ggggccagat ggtaagccct     1080
cccgtatcgt agttatctac acgacgggga gtcaggcaac tatggatgaa cgaaatagac     1140
agatcgctga gataggtgcc tcactgatta agcattggta agtttaaaca gaccacaacg     1200
gtttccctct agcgggatca attccgcccc tctccctccc cccccctaa cgttactggc     1260 cgaagccgct tggaataagg ccggtgtgcg tttgtctata tgttattttc caccatattg     1320
ccgtcttttg gcaatgtgag ggcccggaaa cctggccctg tcttcttgac gagcattcct     1380
aggggtcttt cccctctcgc caaggaatg caaggtctgt tgaatgtcgt gaaggaagca     1440
gttcctctgg aagcttcttg aagacaaaca acgtctgtag cgaccctttg caggcagcgg     1500 aacccccac ctggcgacag gtgcctctgc ggccaaaagc cacgtgtata agatacacct     1560
gcaaaggcgg cacaacccca gtgccacgtt gtgagttgga tagttgtgga aagagtcaaa     1620
tggctctcct caagcgtatt caacaagggg ctgaaggatg cccagaaggt accccattgt     1680
atgggatctg atctgggggcc tcggtgcaca tgctttacat gtgtttagtc gaggttaaaa     1740
aacgtctagg cccccgaac cacggggacg tggttttcct ttgaaaaaca cgataatacc     1800
atggcgccca tcacggccta ctcccaacag acgcggggcc tacttggttg catcatcact     1860
agccttacag gccgggacaa gaaccaggtc gagggagagg ttcaggtggt ttccaccgca     1920
acacaatcct tcctggcgac ctgcgtcaac ggcgtgtgtt ggaccgttta ccatggtgct     1980
ggctcaaaga ccttagccgg cccaaagggg ccaatcaccc agatgtacac taatgtggac     2040
caggacctcg tcggctggca ggcgcccccc ggggcgcgtt ccttgacacc atgcacctgt     2100
ggcagctcag acctttactt ggtcacgaga catgctgacg tcattccggt gcgccggcgg     2160
ggcgacagta gggggagcct gctctccccc aggcctgtct cctacttgaa gggctcttcg     2220
ggtggtccac tgctctgccc ttcggggcac gctgtgggca tcttccgggc tgccgtatgc     2280
acccgggggg ttgcgaaggc ggtggacttt gtgcccgtag agtccatgga aactactatg     2340
cggtctccgg tcttcacgga caactcatcc ccccgccg taccgcagtc atttcaagtg     2400
gcccacctac acgctcccac tggcagcggc aagagtacta aagtgccggc tgcatatgca     2460
gcccaagggc acaaggtgct cgtcctcaat ccgtccgttg ccgctacctt agggtttggg     2520
gcgtatatgt ctaaggcaca cggtattgac cccaacatca gaactggggt aaggaccatt     2580
```

-continued

```
accacaggcg ccccgtcac atactctacc tatggcaagt tcttgccga tggtggttgc    2640 tctgggggcg cttatgacat cataatatgt gatgagtgcc attcaactga ctcgactaca    2700
atcttgggca tcggcacagt cctggaccaa gcggagacgg ctggagcgcg cttgtcgtg    2760 ctcgccaccg ctacgcctcc gggatcggtc accgtgccac acccaaacat cgaggaggtg    2820
gccctgtcta atactggaga gatcccttc tatggcaaag ccatccccat tgaagccatc    2880 aggggggaa ggcatctcat tttctgtcat tccaagaaga agtgcgacga gctcgccgca    2940
aagctgtcag gcctcggaat caacgctgtg gcgtattacc ggggctcga tgtgtccgtc    3000 ataccaacta tcggagacgt cgttgtcgtg gcaacagacg ctctgatgac gggctatacg    3060
ggcgactttg actcagtgat cgactgtaac acatgtgtca cccagacagt cgacttcagc    3120
ttggatccca ccttcaccat tgagacgacg accgtgcctc aagacgcagt gtcgcgctcg    3180
cagcggcggg gtaggactgg caggggtagg atgggcatct acaggtttgt gactccggga    3240
gaacggccct cgggcatgtt cgattcctcg gtcctgtgtg agtgctatga cgcgggctgt    3300
gcttggtacg agctcacccc cgccgagacc tcggttaggt tgcgggccta cctgaacaca    3360 ccaggggttgc ccgtttgcca ggaccacctg gagttctggg agagtgtctt cacaggcctc    3420
acccacatag atgcacactt cttgtcccag accaagcagg caggagacaa cttcccctac    3480
ctggtagcat accaagccac ggtgtgcgcc agggctcagg ccccacctcc atcatgggat    3540
caaatgtgga agtgtctcat acggctgaaa cctacgctgc acgggccaac acccttgctg    3600
tacaggctgg gagccgtcca aaatgaggtc accctcaccc accccataac caaatacatc    3660
atggcatgca tgtcggctga cctggaggtc gtcactagca cctgggtgct ggtgggcgga    3720
gtccttgcag ctctggccgc gtattgcctg acaacaggca gtgtggtcat tgtgggtagg    3780
attatcttgt ccgggaggcc ggctattgtt cccgacaggg agtttctcta ccaggagttc    3840
gatgaaatgg aagagtgcgc ctcgcacctc ccttacatcg agcagggaat gcagctcgcc    3900
gagcaattca gcagaaagc gctcgggtta ctgcaaacag ccaccaaaca agcggaggct    3960
gctgctcccg tggtggagtc caagtggcga gcccttgaga cattctgggc gaagcacatg    4020
tggaatttca tcagcgggat acagtactta gcaggcttat ccactctgcc tgggaacccc    4080
gcaatagcat cattgatggc attcacagcc tctatcacca gcccgctcac cacccaaagt    4140
accctcctgt ttaacatctt ggggggggtgg gtggctgccc aactcgcccc cccagcgcc    4200 gcttcggctt tcgtgggcgc cggcatcgcc ggtgcggctg ttggcagcat aggccttggg    4260
aaggtgcttg tggacattct ggcgggttat ggagcaggag tggccggcgc gctcgtggcc    4320
ttcaaggtca tgagcggcga gatgcccttc ccgaggacc tggtcaatct acttcctgcc    4380
atcctctctc ctggcgccct ggtcgtcggg gtcgtgtgtg cagcaatact gcgtcgacac    4440
gtgggtccgg gagaggggc tgtgcagtgg atgaaccggc tgatagcgtt cgcctcgcgg    4500
ggtaatcatg tttcccccac gcactatgtg cctgagagcg acgccgcagc gcgtgttact    4560
cagatcctct ccagccttac catcactcag ctgctgaaaa ggctccacca gtggattaat    4620
gaagactgct ccacaccgtg ttccggctcg tggctaaggg atgtttggga ctggatatgc    4680
acggtgttga ctgacttcaa gacctggctc cagtccaagc tcctgccgca gctaccggga    4740
gtcccttttt tctcgtgcca acgcgggtac aagggagtct ggcggggaga cggcatcatg    4800
caaaccacct gccatgtgg agcacagatc accggacatg tcaaaaacgg ttccatgagg    4860
atcgtcgggc ctaagacctg cagcaacacg tggcatggaa cattccccat caacgcatac    4920
```

-continued

| | | | | |
|---|---|---|---|---|
| accacgggcc | cctgcacacc | ctctccagcg | ccaaactatt | ctagggcgct gtggcgggtg | 4980 |
| gccgctgagg | agtacgtgga | ggtcacgcgg | gtggggatt | tccactacgt gacgggcatg | 5040 |
| accactgaca | acgtaaagtg | cccatgccag | gttccggctc | ctgaattctt cacggaggtg | 5100 |
| gacggagtgc | ggttgcacag | gtacgctccg | gcgtgcaggc | ctctcctacg ggaggaggtt | 5160 |
| acattccagg | tcgggctcaa | ccaatacctg | gttgggtcac | agctaccatg cgagcccgaa | 5220 |
| ccggatgtag | cagtgctcac | ttccatgctc | accgacccct | cccacatcac agcagaaacg | 5280 |
| gctaagcgta | ggttggccag | ggggtctccc | ccctccttgg | ccagctcttc agctatccag | 5340 |
| ttgtctgcgc | cttccttgaa | ggcgacatgc | actacccacc | atgtctctcc ggacgctgac | 5400 |
| ctcatcgagg | ccaacctcct | gtggcggcag | gagatgggcg | ggaacatcac ccgcgtggag | 5460 |
| tcggagaaca | aggtggtagt | cctggactct | ttcgacccgc | ttcgagcgga ggaggatgag | 5520 |
| agggaagtat | ccgttccggc | ggagatcctg | cggaaatcca | agaagttccc cgcagcgatg | 5580 |
| cccatctggg | cgcgcccgga | ttacaaccct | ccactgttag | agtcctggaa ggacccggac | 5640 |
| tacgtccctc | cggtggtgca | cgggtgcccg | ttgccaccta | tcaaggcccc tccaatacca | 5700 |
| cctccacgga | gaaagaggac | ggttgtccta | acagagtcct | ccgtgtcttc tgccttagcg | 5760 |
| gagctcgcta | ctaagaccct | cggcagctcc | gaatcatcgg | ccgtcgacag cggcacggcg | 5820 |
| accgcccttc | ctgaccaggc | ctccgacgac | ggtgacaaag | gatccgacgt tgagtcgtac | 5880 |
| tcctccatgc | cccccccttga | gggggaaccg | ggggaccccg | atctcagtga cgggtcttgg | 5940 |
| tctaccgtga | gcgaggaagc | tagtgaggat | gtcgtctgct | gctcaatgtc ctacacatgg | 6000 |
| acaggcgcct | tgatcacgcc | atgcgctgcg | gaggaaagca | agctgcccat caacgcgttg | 6060 |
| agcaactctt | tgctgcgcca | ccataacatg | gtttatgcca | caacatctcg cagcgcaggc | 6120 |
| ctgcggcaga | agaaggtcac | cttttgacaga | ctgcaagtcc | tggacgacca ctaccgggac | 6180 |
| gtgctcaagg | agatgaaggc | gaaggcgtcc | acagttaagg | ctaaactcct atccgtagag | 6240 |
| gaagcctgca | agctgacgcc | cccacattcg | gccaaatcca | agtttggcta tggggcaaag | 6300 |
| gacgtccgga | acctatccag | caaggccgtt | aaccacatcc | actccgtgtg gaaggacttg | 6360 |
| ctggaagaca | ctgtgacacc | aattgacacc | accatcatgg | caaaaaatga ggttttctgt | 6420 |
| gtccaaccag | agaaaggagg | ccgtaagcca | gcccgcctta | tcgtattccc agatctggga | 6480 |
| gtccgtgtat | gcgagaagat | ggccctctat | gatgtggtct | ccaccttcc tcaggtcgtg | 6540 |
| atgggctcct | catacggatt | ccagtactct | cctgggcagc | gagtcgagtt cctggtgaat | 6600 |
| acctggaaat | caaagaaaaa | ccccatgggc | ttttcatatg | acactcgctg tttcgactca | 6660 |
| acggtcaccg | agaacgacat | ccgtgttgag | gagtcaattt | accaatgttg tgacttggcc | 6720 |
| cccgaagcca | gacaggccat | aaaatcgctc | acagagcggc | tttatatcgg gggtcctctg | 6780 |
| actaattcaa | aagggcagaa | ctgcggttat | cgccggtgcc | gcgcgagcgg cgtgctgacg | 6840 |
| actagctgcg | gtaacacccct | cacatgttac | ttgaaggcct | ctgcagcctg tcgagctgcg | 6900 |
| aagctccagg | actgcacgat | gctcgtgaac | ggagacgacc | ttgtcgttat ctgtgaaagc | 6960 |
| gcgggaaccc | aagaggacgc | ggcgagccta | cgagtcttca | cggaggctat gactaggtac | 7020 |
| tctgcccccc | ccggggaccc | gccccaacca | gaatacgact | tggagctgat aacatcatgt | 7080 |
| tcctccaatg | tgtcggtcgc | ccacgatgca | tcagcaaaaa | gggtgtacta cctcacccgt | 7140 |
| gatcccacca | cccccctcgc | acgggctgcg | tgggaaacag | ctagacacac tccagttaac | 7200 |
| tcctggctag | gcaacattat | catgtatgcg | cccactttgt | gggcaaggat gattctgatg | 7260 |
| actcacttct | tctccatcct | tctagcacag | gagcaacttg | aaaaagccct ggactgccag | 7320 |

```
atctacgggg cctgttactc cattgagcca cttgacctac ctcagatcat tgaacgactc    7380
catggcctta gcgcattttc actccatagt tactctccag gtgagatcaa tagggtggct    7440
tcatgcctca ggaaacttgg ggtaccgccc ttgcgagctt ggagacaccg ggcccggaat    7500
gtccgcgcta ggcttctgtc cagaggaggc agggctgcca tatgtggcaa gtacctcttc    7560
aactgggcag taaggacaaa gcttaaactc actccaatag cggccgctgg ccggctggac    7620
ttgtccagct ggttcacggc tggctacagc gggggagaca tttatcacgg cgtgtctcat    7680
gcccggcccc gctggttctg gttttgccta ctcctgctcg ctgcaggaat aggcatctac    7740
ctcctcccca atcgatgaag gttggggtaa acactccggc ctcttaggcc atttcctgtg    7800
tttttttttt tttttttttt gtttttttttc tttttttttt tttttttttc tttttccctt    7860 cttcctttc  tctttttttc ttctttaatg gtggctccat cttagcccta gtcacggcta    7920
gctgtgaaag gtccgtgagc cgcatgactg cagagagtgc tgatactggc ctctctgcag    7980
atcatgt                                                             7987
```

<210> SEQ ID NO 4
<211> LENGTH: 7990
<212> TYPE: DNA
<213> ORGANISM: Artificial Sequence
<220> FEATURE:
<223> OTHER INFORMATION: Chimeric HCV Repicon

<400> SEQUENCE: 4

```
gccagccccc gattgggggc gacactccac catagatcac tcccctgtga ggaactactg      60
tcttcacgca gaaagcgtct agccatggcg ttagtatgag tgtcgtgcag cctccaggcc     120
cccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta ccgtgcac catgagcacg aatcctaaac       360
ctcaaagaaa aaccaaaggg cgcgccatgc acccagaaac gctggtgaaa gtaaaagatg     420
ctgaagatca gttgggtgca cgagtgggtt acatcgaact ggatctcaac agcggtaaga     480
tccttgagag ttttcgcccc gaagaacgtt ttccaatgat gagcactttt aaagttctgc     540
tatgtggcgc ggtattatcc cgtattgacg ccgggcaaga gcaactcggt cgccgcatac     600
actattctca gaatgacttg gttgagtact caccagtcac agaaaagcat cttacggatg     660
gcatgacagt aagagaatta tgcagtgctg ccataaccat gagtgataac actgcggcca     720
acttacttct gacaacgatc ggaggaccga aggagctaac cgcttttttg cacaacatgg     780
gggatcatgt aactcgcctt gatcgttggg aaccggagct gaatgaagcc ataccaaacg     840
acgagcgtga caccacgatg cctgtagcaa tggcaacaac gttgcgcaaa ctattaactg     900
gcgaactact tactctagct tcccggcaac aattaataga ctggatggag gcggataaag     960
ttgcaggacc acttctgcgc tcggcccttc cggctggctg gtttattgct gataaatctg    1020
gagccggtga gcgtgggtct cgcggtatca ttgcagcact ggggccagat ggtaagccct    1080
cccgtatcgt agttatctac acgacgggga gtcaggcaac tatggatgaa cgaaatagac    1140
agatcgctga gataggtgcc tcactgatta agcattggta agtttaaaca gaccacaacg    1200
gtttccctct agcgggatca attccgcccc tctccctccc ccccccctaa cgttactggc    1260
cgaagccgct tggaataagg ccggtgtgcg tttgtctata tgttatttc  caccatattg    1320
```

-continued

```
ccgtcttttg gcaatgtgag ggcccggaaa cctggccctg tcttcttgac gagcattcct    1380
aggggtcttt cccctctcgc caaaggaatg caaggtctgt tgaatgtcgt gaaggaagca    1440
gttcctctgg aagcttcttg aagacaaaca acgtctgtag cgacccttg caggcagcgg     1500 aacccccac ctggcgacag gtgcctctgc ggccaaaagc cacgtgtata agatacacct     1560
gcaaaggcgg cacaacccca gtgccacgtt gtgagttgga tagttgtgga aagagtcaaa    1620
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aaacgtctag gcccccgaa ccacgggac gtggttttcc tttgaaaaac acgataatac      1800
atggcgccta ttacggccta ctcccaacag acgcgaggcc tcctagggtg tataatcacc    1860
agcctgactg gccgggacaa aaaccaagtg gagggtgagg tccagatcgt gtcaactgct    1920
acccaaacct tcctggcaac gtgcatcaat ggggtatgct ggactgtcta ccacggggcc    1980
ggaacgagga ccatcgcatc acccaagggt cctgtcatcc agatgtatac caatgtggac    2040
caagaccttg tgggctggcc cgctcctcaa ggttcccgct cattgacacc ctgcacctgc    2100
ggctcctcgg acctttacct ggttacgagg cacgccgacg tcattcccgt gcgccggcga    2160
ggtgatagca ggggtagcct gctttcgccc cggcccattt cctacctaaa aggctcctcg    2220
gggggtccgc tgttgtgccc cgcgggacac gccgtgggcc tattcagggc gcggtgtgc    2280 acccgtggag tggccaaggc ggtggacttt atccctgtgg agaacctaga gacaaccatg    2340 agatccccg tgttcacgga caactcctct ccaccagcag tgcccagag cttccaggtg     2400 gcccacctgc atgctcccac cggcagtggt aagagcacca aggtcccggc tgcgtacgca    2460
gcccagggct acaaggtgtt ggtgctcaac ccctctgttg ctgcaacgct gggctttggt    2520
gcttacatgt ccaaggccca tggggtcgat cctaatatca ggaccggggt gagaacaatt    2580
accactggca gccccatcac gtactccacc tacggcaagt tccttgccga cggcgggtgc    2640
tcaggaggcg cttatgacat aataatttgt gacgagtgcc actccacgga tgccacatcc    2700
atcttgggca tcggcactgt ccttgaccaa gcagagactg cggggcgag attggttgtg     2760 ctcgccactg ctacccctcc gggctccgtc actgtgtccc atcctaacat cgaggaggtt    2820
gctctgtcca ccaccggaga gatcccttc tacggcaagg ctatccccct cgaggtgatc     2880 aagggggaa gacatctcat cttctgtcac tcaaagaaga agtgcgacga gctcgccgcg    2940
aagctggtcg cattgggcat caatgccgtg gcctactacc gcggacttga cgtgtctgtc    3000
atcccgacca gcggcgatgt tgtcgtcgtg tcaaccgatg ctctcatgac tggctttacc    3060
ggcgacttcg actctgtgat agactgcaac acgtgtgtca ctcagacagt cgatttcagc    3120 cttgaccta cctttaccat tgagacaacc acgctccccc aggatgctgt ctccaggact    3180
cagcgccggg gcaggactgg caggggaaag ctaggcatct acagatttgt ggcaccgggg    3240 gagcgccct ccggcatgtt cgactcgtcc gtcctctgtg agtgctatga cgcgggctgt     3300
gcttggtatg agctcacgcc cgccgagact accgttaggc tacgagcgta catgaacacc    3360
ccggggcttc ccgtgtgcca ggaccatctt gaattttggg agggcgtctt tacgggcctc    3420
acccatatag atgcccactt tctatcccag acaaagcaga gtgggagaa ctttccttac    3480 ctggtagcgt accaagccac cgtgtgcgct agggctcaag cccctcccc atcgtgggac    3540 cagatgtgga agtgtttgat ccgccttaaa cccaccctcc atgggccaac accctgcta    3600 tacagactgg gcgctgttca gaatgaagtc accctgacgc acccaatcac caaatacatc    3660
atgacatgca tgtcggccga cctggaggtc gtcacgagca cctgggtgct cgttggcggc    3720
```

| | |
|---|---|
| gtcctggctg ctctggccgc gtattgcctg tcaacaggct gcgtggtcat agtgggcagg | 3780 |
| attgtcttgt ccgggaagcc ggcaattata cctgacaggg aggttctcta ccaggagttc | 3840 |
| gatgagatgg aagagtgctc tcagcactta ccgtacatcg agcaagggat gatgctcgct | 3900 |
| gagcagttca agcagaaggc cctcggcctc ctgcagaccg cgtcccgcca tgcagaggtt | 3960 |
| atcacccctg ctgtccagac caactggcag aaactcgagg tcttctgggc gaagcacatg | 4020 |
| tggaatttca tcagtgggat acaatatttg cgggcctgt caacgctgcc tggtaacccc | 4080 |
| gccattgctt cattgatggc ttttacagct gccgtcacca gcccactaac cactggccaa | 4140 |
| accctcctct tcaacatatt gggggggtgg gtggctgccc agctcgccgc ccccggtgcc | 4200 |
| gctaccgcct ttgtgggcgc tggcttagct ggcgccgcca tcggcagcgt tggactgggg | 4260 |
| aaggtcctcg tggacattct gcagggtat ggcgcggggcg tggcgggagc tcttgtagca | 4320 |
| ttcaagatca tgagcggtga ggtcccctcc acggaggacc tggtcaatct gctgcccgcc | 4380 |
| atcctctcgc ctggagccct tgtagtcggt gtggtctgcg cagcaatact gcgccggcac | 4440 |
| gttggcccgg gcgaggggc agtgcaatgg atgaaccggc taatagcctt cgcctcccgg | 4500 |
| gggaaccatg tttcccccac gcactacgtg ccggagagcg atgcagccgc ccgcgtcact | 4560 |
| gccatactca gcagcctcac tgtaacccag ctcctgaggc gactacatca gtggataagc | 4620 |
| tcggagtgta ccactccatg ctccggctcc tggctaaggg acatctggga ctggatatgc | 4680 |
| gaggtgctga gcgactttaa gacctggctg aaagccaagc tcatgccaca actgcctggg | 4740 |
| attcccttg tgtcctgcca gcgcgggtat aggggggtct ggcgaggaga cggcattatg | 4800 |
| cacactcgct gccactgtgg agctgagatc actggacatg tcaaaaacgg gacgatgagg | 4860 |
| atcgtcggtc ctaggacctg caggaacatg tggagtggga cgttccccat taacgcctac | 4920 |
| accacgggcc cctgtactcc ccttcctgcg ccgaactata agttcgcgct gtggagggtg | 4980 |
| tctgcagagg aatacgtgga gataaggcgg gtggggggact ccactacgt atcgggtatg | 5040 |
| actactgaca atcttaaatg cccgtgccag atcccatcgc ccgaatttttt cacagaattg | 5100 |
| gacggggtgc gcctacatag gtttgcgccc ccttgcaagc ccttgctgcg ggaggaggta | 5160 |
| tcattcagag taggactcca cgagtacccg gtggggtcgc aattaccttg cgagcccgaa | 5220 |
| ccggacgtag ccgtgttgac gtccatgctc actgatccct cccatataac agcagaggcg | 5280 |
| gccgggagaa ggttggcgag agggtcaccc ccttctatgg ccagctcctc ggccatccag | 5340 |
| ctgtccgctc catctctcaa ggcaacttgc accgccaacc atgactcccc tgacgccgag | 5400 |
| ctcatagagg ctaacctcct gtggaggcag gagatgggcg gcaacatcac cagggttgag | 5460 |
| tcagagaaca aagtggtgat tctggactcc ttcgatccgc ttgtggcaga ggaggatgag | 5520 |
| cgggaggtct ccgtacccgc agaaattctg cggaagtctc ggagattcgc ccgggccctg | 5580 |
| cccgtttggg cgcggccgga ctacaacccc cgctagtag agacgtggaa aaagcctgac | 5640 |
| tacgaaccac ctgtggtcca tgctgcccg ctaccacctc cacggtcccc tcctgtgcct | 5700 |
| ccgcctcgga aaaagcgtac ggtggtcctc accgaatcaa ccctatctac tgccttggcc | 5760 |
| gagcttgcca ccaaaagttt tggcagctcc tcaacttccg gcattacggg cgacaatacg | 5820 |
| acaacatcct ctgagcccgc cccttctggc tgccccccg actccgacgt tgagtcctat | 5880 |
| tcttccatgc ccccctgga gggggagcct gggatccgga tctcagcga cgggtcatgg | 5940 |
| tcgacggtca gtagtgggggc cgacacggaa gatgtcgtgt gctgctcaat gtcttattcc | 6000 |
| tggacaggcg cactcgtcac cccgtgcgct gcggaagaac aaaaactgcc catcaacgca | 6060 |

```
ctgagcaact cgttgctacg ccatcacaat ctggtatatt ccaccacttc acgcagtgct    6120
tgccaaaggc agaagaaagt cacatttgac agactgcaag ttctggacag ccattaccag    6180
gacgtgctca aggaggtcaa agcagcggcg tcaaaagtga aggctaactt gctatccgta    6240
gaggaagctt gcagcctgac gcccccacat tcagccaaat ccaagtttgg ctatggggca    6300
aaagacgtcc gttgccatgc cagaaaggcc gtagcccaca tcaactccgt gtggaaagac    6360
cttctggaag acagtgtaac accaatagac actaccatca tggccaagaa cgaggtcttc    6420
tgcgttcagc ctgagaaggg gggtcgtaag ccagctcgtc tcatcgtgtt ccccgacctg    6480
ggcgtgcgcg tgtgcgagaa gatggccctg tacgacgtgg ttagcaaact cccctggcc    6540 gtgatgggaa gctcctacgg attccaatac tcaccaggac agcgggttga attcctcgtg    6600
caagcgtgga agtccaagaa gaccccgatg gggttctcgt atgataccg ctgttttgac    6660 tccacagtca ctgagagcga catccgtacg gaggaggcaa tttaccaatg ttgtgacctg    6720
gacccccaag cccgcgtggc catcaagtcc ctcactgaga ggctttatgt tgggggccct    6780
cttaccaatt caaggggga aaactgcggc tatcgcaggt gccgcgcgag cggcgtactg    6840
acaactagct gtggtaacac cctcacttgc tacatcaagg cccgggcagc ctgtcgagcc    6900
gcagggctcc aggactgcac catgctcgtg tgtggcgacg acttagtcgt tatctgtgaa    6960 agtgcgggg tccaggagga cgcggcgagc ctgagagcct ttacggaggc tatgaccagg    7020
tactccgccc ccccggga ccccacaa ccagaatacg acttggagct tataacatca    7080
tgctcctcca acgtgtcagt cgcccacgac ggcgctggaa aaagggtcta ctaccttacc    7140 cgtgaccta caaccccct cgcgagagcc gcgtgggaga cagcaagaca cactccagtc    7200
aattcctggc taggcaacat aatcatgttt gcccccacac tgtgggcgag gatgatactg    7260
atgacccatt tctttagcgt cctcatagcc agggatcagc ttgaacaggc tcttaactgt    7320
gagatctacg gagcctgcta ctccatgaa ccactggatc tacctccaat cattcaaaga    7380
ctccatggcc tcagcgcatt ttcactccac agttactctc caggtgaaat caataggtg    7440 gccgcatgcc tcagaaaact tggggtcccg ccttgcgag cttggagaca ccgggccgg    7500 agcgtccgcg ctaggcttct gtccagggga ggcagggctg ccatatgtgg caagtacctc    7560
ttcaactggg cagtaagaac aaagctcaaa ctcactccaa tagcggccgc tggccggctg    7620
gacttgtccg gttggttcac ggctggctac agcgggggag acatttatca cagcgtgtct    7680
catgcccggc cccgctggtt ctggttttgc ctactcctgc tcgctgcagg ggtaggcatc    7740
tacctcctcc caaatcgatg aaggttgggg taaacactcc ggcctcttag gccatttcgt    7800
gtcttttttt tgtttttttt tttgtttttt ttcttttttt tttttttttt ttctttttc    7860 cttcttcctt ttctctttt ttcttcttta atggtggctc catcttagcc ctagtcacgg    7920
ctagctgtga aaggtccgtg agccgcatga ctgcagagag tgctgatact ggcctctctg    7980
cagatcatgt                                                          7990
```

METHOD TO CONFER CELL CULTURE REPLICATION ACTIVITY TO DIFFERENT HEPATITIS C VIRUS ISOLATES

CROSS-REFERENCE TO RELATED APPLICATIONS

This application is a 371 National Stage Application of PCT/US2004/003726, with an international filing date of Feb. 9, 2004, and claims the benefit of U.S. Provisional Application No. 60/447,318, filed Feb. 13, 2003, each of which is hereby incorporated by reference.

BACKGROUND OF THE INVENTION

The references cited in the present application are not admitted to be prior art to the claimed invention.

It is estimated that about 3% of the world's population are infected with the Hepatitis C virus (HCV). (Wasley et al., 2000. *Semin. Liver Dis.* 20, 1-16.) Exposure to HCV results in an overt acute disease in a small percentage of cases, while in most instances the virus establishes a chronic infection causing liver inflammation and slowly progresses into liver failure and cirrhosis. (Iwarson, 1994. *FEMS Microbiol. Rev.* 14, 201-204.) Epidemiological surveys indicate HCV plays an important role in hepatocellular carcinoma pathogenesis. (Kew, 1994. *FEMS Microbiol. Rev.* 14, 211-220, Alter, 1995. *Blood* 85, 1681-1695.)

The HCV genome consists of a single strand RNA about 9.5 kb in length, encoding a precursor polyprotein about 3000 amino acids. (Choo et al., 1989. *Science* 244, 362-364, Choo et al., 1989. *Science* 244, 359-362, Takamizawa et al., 1991. *J. Virol.* 65, 1105-1113.) The HCV polyprotein contains the viral proteins in the order: C-E1-E2-p7-NS2-NS3-NS4A-NS4B-NS5A-NS5B.

Individual viral proteins are produced by proteolysis of the HCV polyprotein. Host cell proteases release the putative structural proteins C, E1, E2, and p7, and create the N-terminus of NS2 at amino acid 810. (Mizushima et al., 1994. *J. Virol.* 68, 2731-2734, Hijikata et al., 1993. *Proc. Natl. Acad. Sci. USA* 90, 10773-10777.)

The non-structural proteins NS3, NS4A, NS4B, NS5A and NS5B presumably form the virus replication machinery and are released from the polyprotein. A zinc-dependent 30 protease associated with NS2 and the N-terminus of NS3 is responsible for cleavage between NS2 and NS3. (Grakoui et al., 1993. *J. Virol.* 67, 1385-1395, Hijikata et al., 1993. *Proc. Natl. Acad. Sci. USA* 90, 10773-10777.)

A distinct serine protease located in the N-terminal domain of NS3 is responsible for proteolytic cleavages at the NS3/NS4A, NS4A/NS4B, NS4B/NS5A and NS5A/NS5B junctions. (Barthenschlager et al., 1993. *J. Virol.* 67, 3835-3844, Grakoui et al., 1993. *Proc. Natl. Acad. Sci. USA* 90, 10583-10587, Tomei et al, 1993. *J Virol.* 67, 4017-4026.) RNA stimulated NTPase and helicase activities are located in the C-terminal domain of NS3.

NS4A provides a cofactor for NS3 protease activity. (Failla et al., *J. Virol.* 1994. 68, 3753-3760, De Francesco et al., U.S. Pat. No. 5,739,002.)

NS5A is a highly phosphorylated protein conferring interferon resistance. (De Francesco et al., 2000. *Semin Liver Dis.*, 20(1), 69-83, Pawlotsky 1999. *J. Viral Hepat. Suppl.* 1, 47-48.)

NS5B provides an RNA-dependent RNA polymerase. (De Francesco et al., International Publication Number WO 96/37619, published Nov. 28, 1996, Behrens et al., 1996. *EMBO* 15, 12-22, Lohman et al., 1998. *Virology* 249, 108-118.) An important feature of HCV is its high level of genetic variability, which is believed to be a consequence of the low fidelity of the viral polymerase. This variability is underscored by the identification of six major HCV genotypes (designated 1 through 6), more than fifty subtypes, and numerous quasi-species within each subtype. (Farci et al., 2000. *Sem. Liver Dis.* 20, 103-126.)

Several HCV clones that are infectious in chimpanzees have been described. (Kolykhalov et al., 1997. *Science* 277, 570-574, Yanagi et al., 1998. *Proc. Natl. Acad. Sci. USA* 94, 8738-8743, Hong et al., 1999. *Virology* 256, 36-44.) Isolates based on HCV-con1 and HCV-N have been shown to replicate robustly in cell culture. (Lohmann et al., 1999. *Science* 285, 110-113, Ikeda et al., 2002. *J. Virol.* 76, 2997-3006, Guo et al., 2001. *J. Virol.* 75, 8516-8523.)

Efficient replication in cell culture has been invariably associated with adaptive mutations that dramatically increase the frequency with which replication is established. (Ikeda et al., 2002. *J. Virol.* 76, 2997-3006, Blight et al., 2000. *Science* 290, 1972-1974, Lohman et al., 2001. *J. Virol.* 75, 1437-1449, Kriege et al., 2001. *J. Virol.* 75, 4614-4624.) Adaptive mutations in the HCV-con1 isolate have been localized to various non-structural genes, though substitutions upstream of the interferon sensitivity determining region in NS5A, for example S232I, appear to be the most effective. (Blight et al., 2000. *Science* 290, 1972-1974.) Similarly, a 4 amino acid insertion in NS5A that is not commonly observed in vivo is important for replication in cell culture of the HCV-N isolate. (Ikeda et al., 2002. *J. Virol.* 76, 2997-3006.)

SUMMARY OF THE INVENTION

The present invention features methods for producing HCV replicons using HCV encoding sequences from different isolates. The featured methods are based on the discovered importance of NS3 amino acid position 470 in conferring cell culture replication activity to different HCV isolates.

A HCV replicon is an RNA molecule able to autonomously replicate in a cultured cell, such as Huh7, and produce detectable levels of one or more HCV proteins. The HCV replicon expresses the HCV derived components of the replication machinery and contains cis-elements required for replication in a cultured cell.

Thus, a first aspect of the present invention describes a method of making a HCV replicon having increased replication activity. The method comprises the step of modifying a HCV replicon construct to encode an amino acid substitution at a position corresponding to about 470 of NS3. Modifications in addition to NS3 amino acid 470 may also be introduced. The replicon encoding the NS3 amino acid 470 substitution alone, or in combination with an isoleucine in a position corresponding to amino acid 232 of NS5A has an increased replication activity.

An HCV replicon construct is either a HCV replicon or an HCV replicon intermediate. An HCV replicon intermediate can be modified to produce an HCV replicon.

A "corresponding" position is with respect to SEQ ID NO: 1 or the replicon that encodes SEQ ID NO:1 (i.e., SEQ ID NO:3). The exact amino acid number may vary in different proteins encoded by different replicon constructs. The corresponding position in different constructs can be identified by aligning the relevant regions in the constructs to achieve the greatest degree of homology around the position in question.

Reference to "about" indicates within the approximate position and takes into account variability between different HCV stains. Preferably, "about" is at the same exact position or is at a position one or two amino acids from the exact position.

Reference to "modifying" indicates production of a sequence with one or more differences from a reference or starting sequence. Modifying includes altering one or more nucleotides of a nucleic acid and producing a modified sequence by, for example, nucleic acid synthesis techniques.

Another aspect of the present invention describes a method for identifying a HCV replicon that grows in cell culture. The method involves the steps of:

(a) producing a modified replicon construct encoding an amino acid modification at a position corresponding to about amino acid 470 of NS3, where the modified replicon construct contains an isoleucine in a position corresponding to amino acid 232 of NS5A;

(b) introducing the modified replicon construct into a cell; and (c) measuring replication activity of the modified replicon construct.

Another aspect of the present invention describes a replicon encoding either SEQ ID NO: 1 or SEQ NO: 2. SEQ ID NO: 1 is a HCV NS3-NS4A-NS4B-NS5A-NS5B polyprotein (also referred to as "NS3-NS5B") sequence based on HCV-BK. SEQ ID NO: 2 is a NS3-NS5B HCV sequence based on HCV-H77.

Another aspect of the present invention describes a method of measuring the ability of a compound to affect HCV replicon activity. Measuring can be performed qualitatively or quantitatively. The replicon used in the method is a replicon that is described herein or a replicon that is made using the techniques described herein.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1 illustrates the amino acid sequence SEQ ID NO: 1. The different HCV NS regions are present as follows:
NS3: amino acids 2-632 (NS3 position 470 is underlined);
NS4A: amino acids 633-686;
NS4B: amino acids 687-947;
NS5A: amino acids 948-1394 (NS5A position 232 is underlined); and
NS5B: amino acids 1395-1985.

FIG. 2 illustrates the amino acid sequence SEQ ID NO: 2. The different HCV NS regions are present as follows:
NS3: amino acids 2-632 (NS3 position 470 is underlined);
NS4A: amino acids 633-686;
NS4B: amino acids 687-947;
NS5A: amino acids 948-1395 (NS5A position 232 is underlined); and
NS5B: amino acids 1396-1985.

FIGS. 3A-3D illustrate the nucleotide sequence SEQ ID NO: 3. The different regions are present as follows:
5'-UTR-PC: nucleotides 1-386;
beta-lactamase: nucleotides 387-1181;
EMCV IRES: nucleotides 1225-1800;
NS3: nucleotides 1804-3696 (codon for amino acid NS3 470M is underlined);
NS4A: nucleotides 3697-3858;
NS4B: nucleotides 3859-4641;
NS5A: nucleotides 4642-5982 (codon for amino acid 232I is underlined);
NS5B: nucleotides 5983-7755; and
3'-UTR: nucleotides 7759-7987.

FIGS. 4A-4D illustrate the nucleotide sequence SEQ ID NO: 4. The different regions are present as follows:
5'-UTR-PC: nucleotides 1-386;
beta-lactamase: nucleotides 387-1181;
EMCV IRES: nucleotides 1225-1800;
NS3: nucleotides 1804-3696 (codon for amino acid 470L is underlined);
NS4A: nucleotides 3697-3858;
NS4B: nucleotides 3859-4641;
NS5A: nucleotides 4642-5985 (codon for amino acid 232I is underlined);
NS5B: nucleotides 5986-7758; and
3'-UTR: nucleotides 7762-7990.

DETAILED DESCRIPTION OF THE INVENTION

Figure 5:
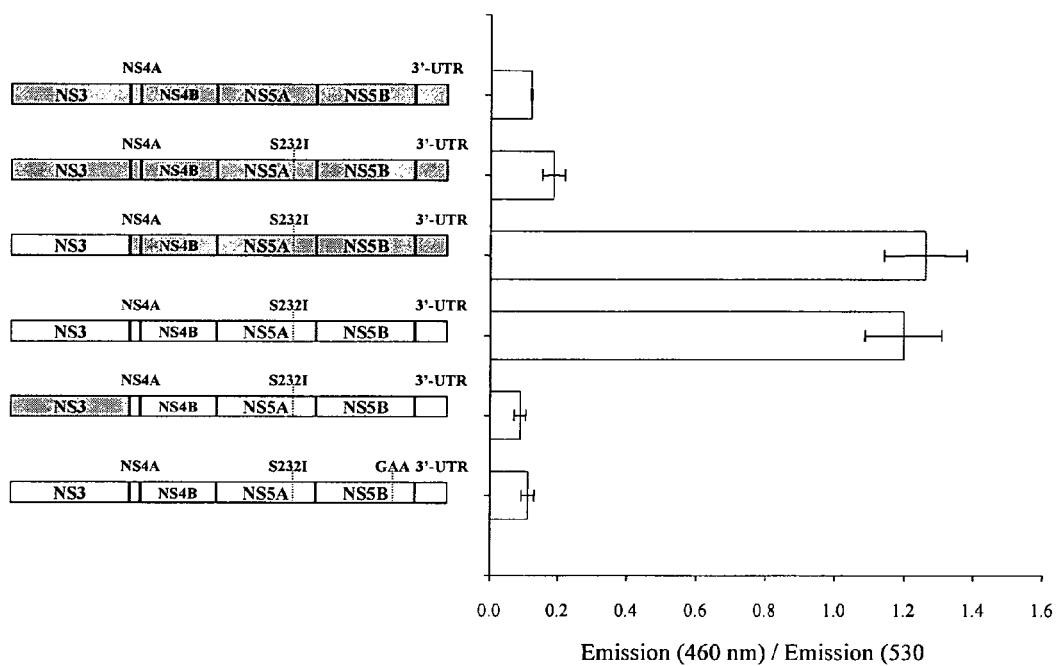
FIG. 5 illustrates subgenomic replicon maps for different replicons and the ability of the replicons to replicate. Huh7 cells were transfected with 5 µg of the indicated replicons and then assayed for replication at day 4. Regions derived from HCV-BK are indicated by the shaded boxes and those from HCV-con1 by the open boxes. Results are averages of three or more independent experiments.

Cell-culture replication activity was found to be enhanced by modifying an amino acid located at position 470 of HCV NS3. HCV NS3 amino acid 470 is present in helicase domain II.

The ability of modifications to NS3 amino acid 470 to enhance replicon activity is illustrated by modifying HCV-BK and HCV-H77. Substitutions in NS3 residue 470 in combination with the NS5A S232I adaptive mutation produced robust cell culture replication to otherwise inactive HCV-BK and HCV-H77 replicons.

Providing cell culture activity to replicons based on different HCV isolates has a variety of different uses such as facilitating identification of broadly efficacious compounds against different HCV isolates and facilitating HCV research. Compounds inhibiting HCV replication have research and therapeutic applications. Therapeutic applications include using those compounds having appropriate pharmacological properties such as efficacy and lack of unacceptable toxicity to treat or inhibit onset of HCV in a patient.

I. HCV Replicon Constructs

HCV replicon constructs that can be modified at a position corresponding to about amino acid 470 of NS3 to increase replicon activity, can be based on different HCV sequences. HCV sequences include naturally occurring sequences, chimeric sequences, and functional variants of such sequences. Functional variants of a natural occurring or a chimeric sequence contain one or more mutations and are able to function as a replicon.

Naturally occurring HCV isolates include those well known in the art and clinical isolates. HCV isolates can be classified into the following six major genotypes comprising one or more subtypes: HCV-1/(1a, 1b, 1c), HCV-2/(2a, 2b, 2c), HCV-3/(3a, 3b, 10a), HCV-4/(4a), HCV-5/(5a) and HCV-6/(6a, 6b, 7b, 8b, 9a, 11a). (Simmonds, 2001. *J. Gen. Virol.,*

82, 693-712.) Examples of HCV sequences have been deposited in GenBank and described in various publications. (See, for example, Chamberlain, et al., 1997. *J. Gen. Virol.*, 78, 1341-1347.)

II. Replicon Components

The basic subunit of an HCV replicon encodes a HCV NS3-NS5B polyprotein along with a suitable 5'-UTR-partial core (PC) region and 3'-UTR. NS3-NS5B may contain different regions from different HCV strains. Additional regions may be present including those coding for HCV proteins or elements such as the complete core, E1, E2, p7 or NS2; and those coding for other types of proteins or elements such as an encephalomyocarditis virus (EMCV) internal ribosome entry site (IRES), a reporter protein, or a selection protein.

The HCV 5'-UTR-PC region provides an IRES for protein translation and elements needed for replication. The HCV 5'-UTR-PC region includes naturally occurring HCV 5'-UTR extending about 36 nucleotides into a HCV core encoding region, and functional derivatives thereof. The IRES and PC can be present in different locations such as a site downstream from a sequence encoding a selection protein, a reporter protein, or an HCV polyprotein.

Functional derivatives of the 5'-UTR-PC region able to initiate translation and assist replication can be designed taking into account structural requirements for HCV translation initiation. (See, for example, Honda et al., 1996. *Virology* 222, 31-42.) The effect of different modifications to a 5'-UTR-PC region can be determined using techniques measuring replicon activity.

In addition to the HCV 5'-UTR-PC region, other types of IRES elements can also be present in a replicon. Other types of IRES elements can be present in different locations including immediately upstream of the region encoding an HCV polyprotein. Examples of non-HCV IRES elements that can be used are the EMCV IRES, poliovirus IRES, and bovine viral diarrhea virus IRES.

The HCV 3'-UTR assists HCV replication. HCV 3'-UTR includes naturally occurring HCV 3'-UTR and functional derivatives thereof. Naturally occurring 3'-UTR's have a poly U tract and an additional region of about 100 nucleotides. (Tanaka et al., 1996. *J. Virol.* 70, 3307-3312, Kolykhalov et al., 1996. *J. Virol.* 70, 3363-3371.) At least in vivo, the 3'-UTR appears to be essential for replication. (Kolykhalov et al., 2000. *J. Virol.* 4, 2046-2051.) Examples of naturally occurring 3' UTR derivatives are described by Bartenschlager International Publication Number EP 1 043 399.

The NS3-NS5B polyprotein encoding region provides for a polyprotein that can be processed in a cell into different proteins. Suitable NS3-NS5B polyprotein sequences that may be part of a replicon include those present in different HCV strains and functional equivalents thereof resulting in the processing of NS3-NS5B to produce functional replication machinery. Proper processing can be measured by assaying, for example, HCV protein production.

An HCV replicon may contain non-HCV sequences in addition to HCV sequences. The additional sequences should not prevent replication and expression, and preferably serve a useful function. Sequences that can be used to serve a useful function include a selection sequence, a reporter sequence, transcription elements and translation elements.

A selection sequence in a HCV replicon facilitates the identification and/or isolation of a cell containing the replicon. Selection sequences providing resistance to an agent that inhibits cell growth can be used in conjunction with selective pressure inhibiting growth of cells not containing the selection sequence. Examples of selection sequences include sequences encoding antibiotic resistance, and ribozymes; and reporters compatible with cell sorting such as green fluorescence protein and beta-lactamase.

Antibiotic resistance can be used in conjunction with an antibiotic to select for cells containing replicons. Examples of selection sequences providing antibiotic resistance are sequences encoding resistance to neomycin, hygromycin, puromycin, or zeocin.

A ribozyme serving as a selection sequence can be used in conjunction with an inhibitory nucleic acid molecule preventing cellular growth. The ribozyme recognizes and cleaves the inhibitory nucleic acid.

A reporter sequence can be used to detect replicon replication or protein expression. Preferred reporter proteins are enzymatic proteins whose presence can be detected by measuring product produced by the protein. Examples of reporter proteins include luciferase, beta-lactamase, secretory alkaline phosphatase, beta-glucuronidase, green fluorescent protein and its derivatives. In addition, a reporter nucleic acid sequence can be used to provide a reference sequence that can be targeted by a complementary nucleic acid probe. Hybridization of the complementary nucleic acid probe to its target can be determined using standard techniques.

Replicons containing reporter sequences may or may not also contain a selection sequence. Selection sequences providing resistance to an agent inhibiting cell growth can be used in conjunction with selective pressure to select for cells maintaining the replicon.

Additional sequences can be part of the same cistron as the HCV polyprotein or can be a separate cistron. If part of the same cistron, additional sequences coding for a protein should result in a product that is either active as a chimeric protein or is cleaved inside a cell so it is separated from HCV protein.

Selection and reporter sequences encoding a protein when present as a separate cistron should be associated with elements needed for translation. Such elements include an IRES 5' to the selection or reporter sequence.

A preferred construct is a bicistronic replicon, where one cistron encodes for a selection or reporter sequence and the second cistron encodes for HCV proteins. More preferably, the first cistron contains a HCV 5'-UTR-PC region joined to the selection or reporter sequence; and the second cistron contains the EMCV internal ribosome entry site, NS2-NS5B or NS3-NS5B, and a 3'-UTR.

The production and use of HCV replicons, and the effect of different mutations on replicon activity are described in different references. (See, for example, Lohmann et al., 1999. *Science* 285, 110-113, Bartenschlager, European Patent Application 1 043 399, published Oct. 11, 2000, Blight et al., 2000. *Science* 290, 1972-1974, Lohmann et al., 2001. *Journal of Virology* 75, 1437-1449, Pietschmann et al., 2001. *Journal of Virology* 75, 1252-1264, Rice et al., International Publication Number WO 01/89364, published Nov. 29, 2001, Bichko International Publication Number WO 02/238793, published May 16. 2002, Kukolj et al., International Publication Number WO 02/052015, published Jul. 4, 2002, De Francesco et al., International Publication Number WO 02/059321, published Aug. 1, 2002.)

In a preferred embodiment, HCV replicons containing a modification At a position corresponding to amino acid 470 of NS3 also contains an adaptive mutation corresponding to the NS5A S232I mutation described by Blight et al. (Blight et al. 2000. *Science* 290, 1972-1974). Replicons may contain additional mutations. Examples of additional mutations and techniques for identifying adaptive mutations are noted in different references such as those concerning the effect of different mutations on replicon activity.

III. Replicon Modification

Replicon construct modifications can be achieved by different techniques such as altering one or more nucleotides present on a nucleic acid and by synthesizing a nucleic acid sequence to be different from a reference sequence. Modifications to a nucleic acid are one or more of the following: addition(s), substitution(s), and deletion(s). Techniques for altering nucleotides and synthesizing nucleic acid are well known in the art. (Ausubel, *Current Protocols in Molecular Biology*, John Wiley, 1987-1998, and Sambrook et al., *Molecular Cloning, A Laboratory Manual*, $2^{nd}$ Edition, Cold Spring Harbor Laboratory Press, 1989.) Modifications to a particular location in a construct sequence can be achieved by first identifying a corresponding position. A corresponding location is identified using SEQ ID NO: 1 as a reference sequence. The corresponding position can be identified by aligning the relevant regions in the construct and reference sequence to achieve the greatest degree of homology around the position in question.

Maximum homology is the alignment providing the least number of total amino acid differences. Amino acid differences include addition(s), substitution(s), and deletion(s).

An example of determining the location of a position corresponding to amino acid 470 of NS3 in a replicon construct is as follows:

a) use SEQ ID NO: 1 as a reference sequence;

b) align the reference sequence and construct sequence to achieve maximum homology around NS3 amino acid 470 of the reference sequence. The alignment preferably involves amino acids 460 to 480 of SEQ ID NO: 1 (about 10 bases on either side of the identified position); and c) identify the amino acid in the construct located in the position aligned with NS3 amino acid 470 of the reference sequence.

After identifying the corresponding location, nucleic acid encoding the modified replicon can be produced by techniques such as mutating a nucleic acid or synthesizing a nucleic acid. Nucleic acid encoding a particular amino acid sequence can be obtained taking into account the genetic code. Amino acids are encoded by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU.

The effect of a particular modification can be evaluated by producing a replicon construct containing elements needed for replication. Preferably, a bicistronic replicon is employed. Replicon activity can be measured using techniques such those described in references dealing with adaptive mutations (Section II. supra.), and those described in the Examples infra.

IV. Resistance Phenotyping

Resistance phenotyping can be performed to determine the effect of a particular compound on different HCV isolates. The guidance provided herein can be employed to confer replication activity to replicons based on different HCV isolates. Resistance phenotyping can also be performed using a replicon as a template for producing chimeric replicons.

Chimeric HCV replicons contain HCV regions from different HCV strains. Preferably, the template contains a HCV-1a 3' UTR Bases 7759-7987 of SEQ ID NO: 3 and bases 7762-7990 of SEQ ID NO: 4 provide the nucleotide sequence of the HCV-1a 3' UTR. HCV regions that can be transferred to a template and analyzed include HCV encoded enzymes such as NS2/3 protease, NS3 protease, NS3 helicase, and NS5B, as well as polynucleotide regions important for HCV replication.

V. Host Cells

Preferred cells for use with a HCV replicon are Huh-7 cells and Huh-7 derived cells. "Huh-7 derived cells" are cells produced starting with Huh-7 cells and introducing one or more phenotypic and/or genotypic modifications.

Huh-7 derived cells include replicon enhanced cells produced from Huh-7. Replicon enhanced cells can be obtained by introducing a replicon into a cell, selecting for cells supporting replicon activity, and completely or partially curing the cells of the replicon. The cured or partially cured cells can be used as a host for introducing another replicon.

Preferably, replicon enhanced cells contain a first HCV replicon having a drug resistance gene and a second HCV replicon having a reporter. The first replicon is present in an amount (copy number) compatible with efficient replication of the second HCV replicon. The combination of the two replicons in a replicon enhanced cell is particularly useful for high throughput screening.

Different HCV replicons can be constructed for use as the first replicon. A drug resistance gene can be used to isolate cells supporting replication of the first replicon. Alternatively, the first replicon can encode a reporter gene compatible with cell sorting allowing isolation of cells that support replication of the first replicon.

The first replicon, if present in a cell containing the second replicon, should be present in an amount compatible with efficient replication of the second HCV replicon. The enhanced phenotype of a replicon enhanced cell can be masked or inhibited if the copy number of the first replicon is too high.

If needed, the copy number of the first replicon can be reduced by treating cells with inhibitors of HCV replication or by using cell culture conditions that are not compatible with replicon replication. The latter includes maintaining the cells at high cell densities for prolonged periods of time. The second replicon can be used to monitor HCV replication in enhanced cells.

Inhibitors of HCV replicon replication include IFN-α and HCV inhibitor compounds targeting a HCV protein.

Examples of HCV inhibitory compounds are described in Llinas-Brunet, et al., 2000. *Bioorg Med Chem. Lett.* 10(20), 2267-2270.

Different HCV replicons can be constructed for use as the second replicon. The second replicon in addition to containing an HCV sequence preferably contains a reporter sequence. More preferably, the second replicon contains a reporter sequence such as beta-lactamase, beta-galactosidase, green fluorescence protein or luciferase.

VI. Detection Methods

Methods for detecting replicon activity include those measuring the production or activity of replicon RNA and encoded protein. Measuring can be by qualitative or quantitative analysis. Preferably, replicon activity is measured using a reporter protein.

Preferred reporters are beta-lactamases and luciferases. Beta-lactamases are enzymes catalyzing the cleavage of the beta-lactam ring present in cephalosporins. Different naturally occurring beta-lactamases and functional derivatives of naturally occurring beta-lactamases are well known in the art. (For example, see, Ambler, *Phil. Trans R. Soc. Lond. Ser.* B. 1980.289, 321-331, Kadonaga et al., 1984. *J. Biol. Chem.* 259, 2149-2154, and U.S. Pat. No. 5,744,320.) p Intracellular beta-lactamase activity is preferably measured using a fluorogenic substrate that is cleaved by beta-lactamase. Preferred substrates are membrane permeant fluorogenic substrates that become membrane impermeant inside a cell, and that are cleaved by beta-lactamase to produce a detectable signal. Examples of such substrates are provided in Zlokarnik et al., 1998. *Science* 279, 84-88, and Tsien et al., U.S. Pat. No. 5,741,657.

Beta-lactamase activity can be measured, for example, using a cell-permeant fluorescent beta-lactamase substrate such as CCF2-AM or CCF4-AM (Aurora Biosciences, Inc., San Diego, Calif.). These substrates contain an ester group facilitating transport across the cell membrane. Inside the cell, the ester group is cleaved rendering the substrate membrane impermeant. The intact substrates when stimulated with light of ~405 nm, emit green fluorescence (~530 nm) due to resonant energy transfer from a coumarin to fluorescein dye molecule. Cleavage of the substrate by beta-lactamase disrupts the resonance energy transfer and, the fluorescence emission changes to a blue color (~460 nm) of only the coumarin. The fluorescence emissions of the substrate present in the cells can be detected by, for example, fluorescence microscopy or by a fluorometer in conjunction with appropriate emission and excitation filters.

Beta-lactamase inhibitors such as clavulanic acid can be used to enhance a beta-lactamase reporter system by being present throughout the assay. For example, clavulanic acid being present throughout an assay involving an HCV replicon beta-lactamase reporter sensitizes the assay towards HCV replication inhibitors.

Beta-lactamase activity can be measured, for example, by direct visualization of cells using a fluorescence microscope. Quantitation of HCV replication can be accomplished using a CCD camera acquiring digital images and suitable software quantitating the number of blue and green cells present in such images. T his method quantitates the number of cells in a population harboring HCV replicons expressing beta-lactamase and this measurement is typically expressed as percentage blue cells (% Blue cells).

Another method for measuring beta-lactamase activity employs a fluorescence plate reader that quantitates the amount of green (~530 nm) or blue (~460 nm) fluorescence emitted by cells stimulated with light of ~405 nm. This method can be used for high throughput screening.

Quantitation of beta-lactamase activity can also be accomplished by FACS. This method quantitates the number of blue and green cells in a given cell population as well as the amount of blue and green fluorescence. Instruments capable of cell sorting can be used to isolate cells harboring HCV replicons expressing beta-lactamase.

Techniques suitable for measuring RNA production include those detecting the presence or activity of RNA. RNA can be detected using, for example, complementary hybridization probes or quantitative PCR. Techniques for measuring hybridization between complementary nucleic acids and quantitative PCR are well known in the art. (See for example, Ausubel, *Current Protocols in Molecular Biology*, John Wiley, 1987-1998, Sambrook et al., *Molecular Cloning, A Laboratory Manual*, $2^{nd}$ Edition, Cold Spring Harbor Laboratory Press, 1989, and U.S. Pat. No. 5,731,148.)

RNA enzymatic activity can be provided to the replicon by using a ribozyme sequence. Ribozyme activity can be measured using techniques detecting the ability of the ribozyme to cleave a target sequence.

Techniques measuring protein production include those detecting the presence or activity of a produced protein. The presence of a particular protein can be determined by, for example, immunological techniques. Protein activity can be measured based on the activity of an HCV protein or a reporter protein sequence.

Techniques for measuring HCV protein activity vary depending upon the protein that is measured. Techniques for measuring the activity of different non-structural proteins such as NS2/3, NS3, and NS5B, are well known in the art. (See, for example, references provided in the Background of the Invention.)

Assays measuring replicon activity also include those detecting virion production from a replicon producing a virion; and those detecting a cytopathic effect from a replicon producing proteins exerting such an effect. Cytopathic effects can be detected by assays suitable to measure cell viability.

Assays measuring replicon activity can be used to evaluate the ability of a compound to modulate HCV activities. Such assays can be carried out by providing one or more test compounds to a cell expressing a HCV replicon and measuring the effect of the compound on replicon activity. If a preparation containing more than one compound modulates replicon activity, individual compounds or smaller groups of compounds can be tested to identify replicon active compounds.

VII. Examples

Examples are provided below further illustrating different features of the present invention. The examples also illustrate useful methodology for practicing the invention. These examples do not limit the claimed invention.

Example 1

Materials and Methods

This example describes different materials and methods that were employed to identify amino acids important for replicon activity and to produce replicons.

Cell Culture

Huh7 human hepatoma cells were grown in Dulbecco's modified minimal essential medium (Cellgro) supplemented with 2 mM Glutamax, non-essential amino acids, 100 u/ml penicillin, 100 μg streptomycin, and 10% heat-inactivated fetal bovine serum (Gibco-BRL). Media for culture of cell lines harboring replicon expressing neomycin phosphotransferase were supplemented with G418 as indicated. Cells were grown at 37° C. and 5% $CO_2$ and passaged twice per week.

Replicon Constructs

Standard protocols were used for all manipulation of nucleic acids. Bla-replicon constructs were derived from pHCVneo17.wt (Mottola et al., 2002. *Virology* 293, 31-43), a template for T7 transcription of RNA was identical in sequence to the replicon $_{137}$7neo/NS3-3'/wt (Lohmann et al., 2000. *Science* 285, 110-113.). The beta-lactamase coding region was PCR amplified using pcDNA3-blaM (Aurora Biosciences) as template with primers that introduced Asc I and Pme I sites at the 5'- and 3'-ends, respectively, and subcloned into the corresponding sites of pHCVneo17.wt. A silent mutation was subsequently introduced to eliminate a Sca I restriction site from the bla coding region. The cell culture adaptive mutation S2204I (amino acid position 232 of NS5A) was introduced by PCR mutagenesis using the QuickChange PCR Mutagenesis kit (Stratagene).

The HCV-BK subgenomic replicon was constructed by replacing the NS3 through 3'-UTR sequence of the HCV-con1 replicon with the corresponding region from HCV-BK. The HDV ribozyme was added to the 3'-ends of both the HCV-con1 and HCV-BK replicons to facilitate generation of native 3'-ends (Wang et al., 1986. *Nature (London)* 323, 508-514). In addition, a unique Cla I restriction site has been introduced at the NS5B-3'-UTR junction. Mutations were introduced as indicated using the QuickChange PCR Mutagenesis kit (Stratagene).

Replication Assays

Replicon RNAs were transcribed from templates that were linearized by digestion with the Xba I restriction endonuclease which cleaves downstream of the HDV ribozyme. RNA was transcribed using a commercially available transcription kit (MEGAscript™ T7 kit; Ambion, Inc., Austin, Tex.), treated with DNAse I for 30 minutes to digest template, and then purified using a commercially available RNA purification kit (RNeasy Mini kit; QIAGEN Inc., Valencia, Calif.). Integrity of the transcribed RNAs was checked by analytical agarose gel electrophoresis, and RNA was quantitated by absorbance.

For transient replication assays, Huh7 cells were plated at $2.5\text{-}3 \times 10^5$ cells/well in 6-well tissue culture plates and allowed to adhere overnight. Cells were lipo-transfected with DMRIE-C at the indicated concentrations of bla-replicon RNA for 6-8 hours and then incubated overnight. To assay for expression of the beta-lactamase reporter, medium was removed and cells were stained for 90 minutes with CCF4-AM (Aurora Biosciences Corp.) in DMEM supplemented with 25 mM HEPES, pH 8.0. For quantitation of the fraction of cells harboring bla-replicons, cells were photographed using a digital CCD color camera and green and blue cells were counted by digital image processing (DIP) using Image-Pro Plus software. Alternatively, fluorescence was measured using a CytoFluor 4000 Fluorescence plate reader. Cells were stained 16-24 hours after transfection to determine transfection efficiency.

Cells were split 1:6 and then assayed at day 3 or day 4 for replication by staining for beta-lactamase expression and quantitating either the fraction of cells that harbored replicon by digital image processing or by measuring fluorescence using a fluorescence plate reader.

For colony formation assays, $2 \times 10^5$ cells were transfected with the indicated neo-replicon RNA using DMRIE-C. Medium for selection experiments was supplemented with 250 μg/ml G418. Colonies were counted three to four weeks after transfection.

Purification, Reverse Transcription, and Sequencing of Viral and Replicon RNAs

HCV RNA was isolated from chimpanzee serum using the RNeasy RNA purification kit (Qiagen), and total RNA was purified from $10^6$ replicon harboring cells by Trizol (Gibco) extraction followed by spun-column purification using the RNeasy RNA purification kit. cDNAs comprising the NS3 region were generated by reverse transcription using Superscript II reverse transcriptase (Gibco). cDNAs were subsequently amplified with Expand High Fidelity polymerase, subcloned into pSTBlue1 (Novagen), and then sequenced with an ABI 373 Sequencer.

NS3 Helicase Expression and Purification

NS3 helicases were subcloned into the Bam HI and Hind III restriction sites of pET-21B and expressed in BL21(DE3) cells. NS3 helicases were isolated from clarified bacterial lysates in three steps using immobilized metal affinity chromatography, Q-sepharose (Amersham Pharmacia) chromatography, and poly-U sepharose column chromatography. Purified helicases were stored at −20° C. in 20 mM tris, pH 7.0, 10% glycerol. Protein concentrations were determined by absorbance at 280 nm using a calculated molar extinction coefficient of 47480 $M^{-1}$ $cm^{-1}$.

NS3 Helicase Unwinding Assays

The $^{32}P$ end-labeled partial duplex DNA helicase substrate was prepared essentially as described by Levin et al., 1999. *J. Biol. Chem.* 274, 31839-31846. Unwinding assay reactions were performed in 20 μl and contained 25 mM MOPS, pH 6.5, 3 mM $MgCl_2$, 2 mM DTT, 100 μg/ml BSA, 2 nM substrate, and 10 nM helicase. Helicase and substrate were preincubated for 15 minutes at 25° C. prior to initiating the reaction by adding ATP to 5 mM. Reactions were stopped at various times by the addition of 5 μl of 5× termination mix. Products were resolved using 10% acrylamide TBE gels and quantified by densitometric scanning with a Storm 860 PhosphoImager and ImageQuant software (Molecular Dynamics).

Example 2

In Vivo Replication

HCV-BK based nucleic acid was produced to contain the genotype 1b BK sequence from the 5'-UTR through the Kpn I restriction site in NS5B derived from a Japanese patient (Takamizawa et al., 1991. *J. Virol.* 65, 1105-1113), and a 3'-UTR (genotype 1a) derived from an Italian patient. The HCV-BK based nucleic acid was transcribed and injected into chimpanzees. Direct intrahepatic injection of the in vitro transcribed HCV BK RNA caused HCV infection in chimpanzees. Inoculation of a second chimpanzee with serum from an HCV BK infected chimpanzee also resulted in infection demonstrating that the BK sequences used in this study are infectious.

Example 3

Subgenomic HCV-BK Replicons

Replicon constructs comprising the NS3 through NS5B non-structural genes and the 3'-UTR from HCV BK were tested for cell-culture replication and found not to have significant replication activity. The constructs were engineered with an HDV ribozyme, which auto-catalytically cleaves itself from the 3'-end of the replicon to yield replicon RNA transcripts with native 3'-ends. HCV-con1 replicons transcribed with the HDV ribozyme show the same replication activity as replicons transcribed from a Sca I digested template without the ribozyme.

Replicons were generated either with the beta-lactamase (bla) reporter for transient replication assays or with the neomycin phosphotransferase gene for selection experiments. In addition, the S232I mutation in NS5A that confers cell-culture adaptation to the HCV-con1 replicon (Blight et al., 2000. Science 290, 1972-1974) was engineered into the HCV-BK based replicon.

The wild type replicon derived from the BK chimpanzee-infectious genome replicates very poorly in the transient replication assay (FIG. 5). The activity of the HCV-BK replicon containing the S232I mutation is not significantly different than that of the replication deficient HCV-con1 replicon (GAA mutation) indicating that this adaptive mutation does not confer replication competence to HCV-BK based replicons (FIG. 5).

Similar analyses were performed using a colony formation assay and corresponding neo$^r$ replicons. The wild-type HCV-BK replicon did not yield any colonies. Introduction of the S232I adaptive mutation conferred modest replication competence to HCV-BK (~100 colonies/μg) compared to corresponding HCV-con1 replicons (~5000 colonies/μg). These results indicate that the introduction of only the NS5A-S232I adaptive mutation is not sufficient to confer robust replication competence to the HCV-BK based replicon.

Example 4

Identification of HCV-BK Replication Block

Regardless of the assay format used, HCV-BK replicons failed to replicate efficiently in Huh7 cells either with or without the S232I NS5A adaptive mutation. To identify the block to replication in the BK replicons, chimeras were constructed in which the various non-structural proteins of HCV-BK and HCV-con1 were swapped. These swaps were initially made using HCV-BK replicons that had S232I since this mutation modestly improved BK replicon replication.

As shown in FIG. 5, replacement of the NS3 coding region in the BK replicon with the con1 NS3 resulted in a replicon replicating with essentially the same activity as the HCV-con1 replicon with the NS5A S232I mutation. Conversely, introduction of the HCV-BK NS3 into the HCV-con1 replicon essentially abolished replication activity FIG. 5). In contrast, none of the other con1 regions yielded any improvement in replication of the HCV-BK replicon (data not shown).

The results obtained from the chimera experiments demonstrate that the block to HCV-BK replication in cell culture maps to NS3. An alignment of the HCV-BK and HCV-con1 sequences revealed that there are 12 amino acid differences in NS3 with one mutation mapping to the protease domain and the remaining eleven mapping to the helicase domain.

To identify the amino acid differences accounting for the dramatic changes in replication efficiency, each of the residues in the HCV-BK NS3 differing from that in HCV-con1 were individually mutated to the residue found in HCV-con1. The resulting replicons were then tested for replication activity by Bla-Rep.

Figure 6:
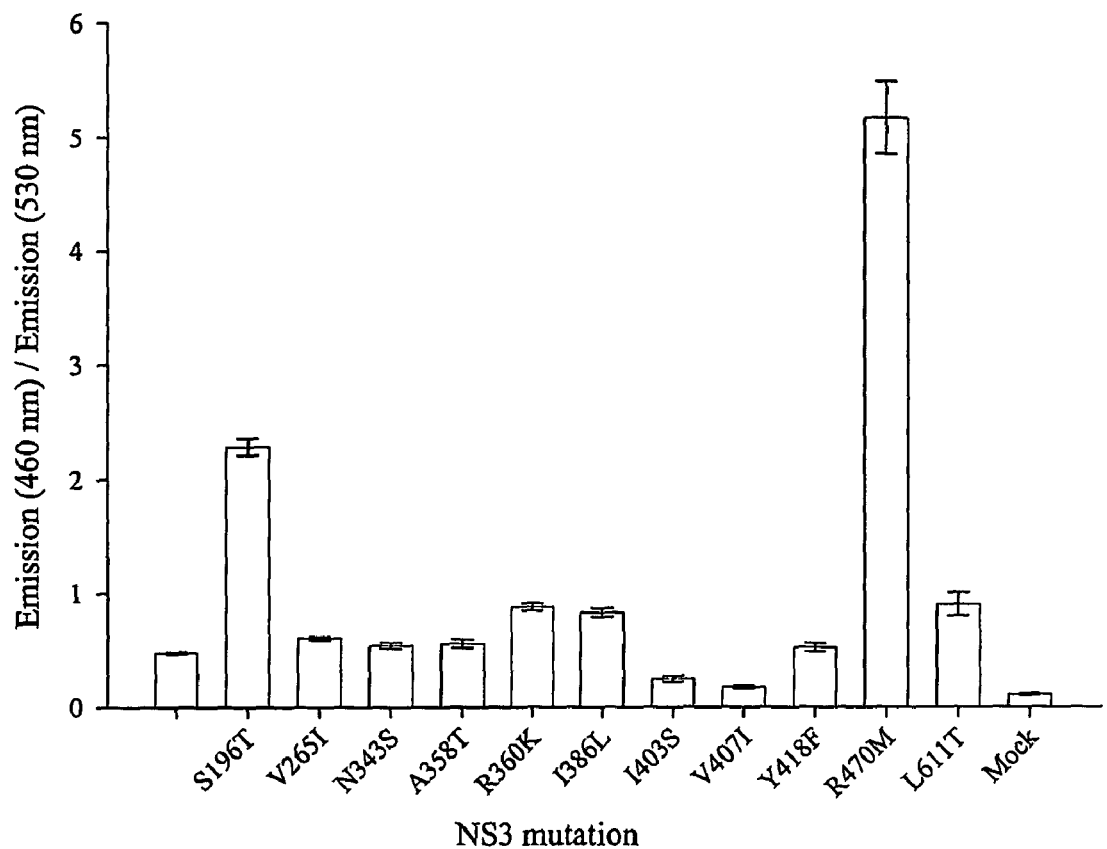
FIG. 6 illustrates the effects of different mutations in NS3 on HCV-BK replicon cell-culture replication. All constructs contain the S232I mutation in NS5A.

As shown in FIG. 6, two mutations provided significant enhancement of replication activity. Introduction of R470M mutation into the HCV-BK NS3 helicase resulted in a replicon with significantly higher replication efficiency than the HCV-con1 S232I replicon. The NS3-S196T mutation also enhanced HCV-BK replicon activity but with lower efficiency than the R470M mutation. At all other positions tested, introduction of the corresponding con1 residue had only modest effects. When the NS3-S196T and R470M mutations were combined, modest but reproducible additivity in transduction efficiency was observed (data not shown).

Although the NS3-R470M mutation dramatically enhances replication activity of HCV-BK replicons, different residues are observed at this position in clinical isolates. To determine whether arginine at this position is incompatible with replication or rather that the methionine at this position is unique in conferring cell-culture replication competence, HCV-BK replicons containing R470P and R470G mutations were tested. Proline, glycine, and leucine are frequently seen in genotype 1 HCV isolates at this position (Table I). As shown in Table II, replicons containing either proline or glycine in place of R470 replicated albeit not as robustly as those with methionine at this position.

TABLE I

Variability of HCV NS3 helicase at position 470.

| Residue | Frequency |
| --- | --- |
| R | 44 |
| G | 28 |
| L | 27 |
| P | 20 |
| S | 16 |
| A | 10 |
| M | 8 |
| H | 7 |
| I | 2 |
| T | 2 |
| Q | 1 |

TABLE II

R470G and R470P in NS3 helicase are compatible with efficient replication.

| Replicon | Em (460 nm)/Em (530 nm) |
| --- | --- |
| HCV-BK (NS5A-S232I) | 0.45 ± 0.03 |
| +NS3-R470M | 3.94 ± 0.22 |
| +NS3-R470G | 2.78 ± 0.22 |
| +NS3-R470P | 2.14 ± 0.25 |
| HCV-con1 (NS5A-S232I; NS5B-GAA) | 0.29 ± 0.07 |

To assess the effect of BK residues at position 196 and 470 on HCV-con1 replication fitness, corresponding HCV-con1 replicons were engineered to have the T196S, M470R, or both mutations and were tested in Bla-Rep. As shown in Table III, the effects of these mutations on HCV-con1 replication was the converse with T196S and M470R causing a modest and dramatic reduction in replication activity, respectively, while the combination of both mutations essentially abrogated replication activity. These results demonstrate that residues 196 and 470 also influence replication of HCV-con1 replicons.

TABLE III

Residues present at positions 196 and 470 in HCV-BK NS3 attenuate replication of the HCV-con1 replicon.

| Replicon | Em (460 nm)/Em (530 nm) ± S.E.M. |
|---|---|
| HCV-con1 (NS5A-S232I) | 2.57 ± 0.18 |
| +T196S | 1.51 ± 0.18 |
| +M470R | 0.78 ± 0.07 |
| +T196S + M470R | 0.41 ± 0.03 |
| HCV-con1 (NS5A-S232I; NS5B-GAA) | 0.29 ± 0.07 |

Example 5

Preferred Amino Acid Combination

The S232I adaptive mutation in NS5A had minimal effects on the replication competence of the BK replicon, but robust replication of BK replicons was observed when this mutation was combined with R470M and to a lesser extent with S196T NS3 helicase mutations. The corresponding replicons without the S232I mutation in NS5A were tested in transient replication assays to assess the importance of S196T and R470M helicase mutations.

HCV BK replicons containing S196T and R470M helicase mutations but not the S232I NS5A adaptive mutation did not efficiently replicate (Table IV.). Additional analyses using a colony formation assay also indicated that residue 470 makes a significantly greater contribution to replication activity than residue 196 (Table IV).

TABLE IV

| Replicon | Bla-Rep assay Em (460 nm)/Em (530 nm) | Colony formation assay |
|---|---|---|
| HCV-BK (WT) | 0.33 ± 0.12 | 0 |
| +NS3-S196T | 0.20 ± 0.09 | 100 |
| +NS3-R470M | 0.29 ± 0.05 | 0 |
| +NS5A-S232I | 0.51 ± 0.07 | 0 |
| +NS5A-S232I + NS3-S196T | 2.05 ± 0.08 | 55 |
| +NS5A-S232I + NS3-R470M | 4.31 ± 0.14 | 22400 |
| HCV-con1 (NS5A-S232I + NS5B-GAA) | 0.28 ± 0.23 | 0 |

Example 6

HCV-H77 Replicons

NS3 helicase domain mutations at positions 196 and 470 confer replication competence to HCV-H77 (genotype 1a) replicons. Like HCV-BK, the genotype 1a isolate HCV-H77 is an example of an infectious clone that fails to replicate efficiently in cell culture with the introduction of the single adaptive mutation S232I in NS5A. (Kolykhalov et al., 1997. *Science* 277, 570-574, Blight et al., 2000. *Science* 290, 1972-1974.)

"Wild-type" HCV-H77 NS3 helicase has a serine at position 196 and a proline at position 470, a combination that is compatible with efficient replication in HCV-BK replicons. A series of HCV-H77 replicons containing either the wild-type serine or a threonine at position 196 and either the wild-type proline, or methionine or leucine at position 470 in NS3 with and without the S232I adaptive mutation in NS5A were generated. These replicons were assayed by Bla-Rep and the data are summarized in Table V.

TABLE V

| Replicon | Em (460 nm)/Em (530 nm) |
|---|---|
| HCV-H77 (NS5A-S232I) | 0.22 ± 0.01 |
| +NS3-S196T | 0.14 ± 0.03 |
| +NS3-P470M | 0.25 ± 0.03 |
| +NS3-S196T + NS3-P470M | 0.25 ± 0.00 |
| +NS3-P470L | 0.50 ± 0.06 |
| +NS3-S196T + NS3-P470L | 0.73 ± 0.13 |
| HCV-con1 (NS5A-S232I + NS5B-GAA | 0.21 ± 0.02 |

As with HCV-BK, efficient replication of HCV-H77 replicons required the S232I adaptive mutation irrespective of which additional mutations were present in NS3. The H77 replicon containing S196 and P470 failed to replicate as did replicons containing the point mutations S196T and P470M in combination with S232I. However, HCV-H77 replicons containing P470L showed a significant enhancement in replication thus demonstrating the importance of this region of NS3 helicase in the cell-culture adaptation of HCV-H77. Although the S196T had essentially no effect in isolation, introduction of this mutation into the HCV-H77 replicon containing P470L further enhanced replication activity. These data indicate that NS3 helicase residues at position 196 and 470 influence the replication potential of genotype 1a replicons.

Example 7

NS3 Helicase Mutations do not Affect Helicase Unwinding Activity

To explore the effects of the cell-culture adaptive mutations on helicase unwinding activity, HCV-BK NS3 helicase domains with and without the S196T and R470M mutations were expressed and purified to homogeneity from *E. coli*. Helicases were then compared in unwinding assays using double stranded DNA substrates. As shown in Table VI, rates of unwinding were comparable for each protein. This together with the fact that both NS3 mutations map to the protein surface suggest that these mutations might mediate interactions with other viral or host encoded proteins involved viral replication.

TABLE VI

| Helicase | Rate (min$^{-1}$ × 10$^3$) |
|---|---|
| Wild-type | 1.16 |
| S196T | 0.91 |
| R470M | 1.29 |

Other embodiments are within the following claims. While several embodiments have been shown and described, various modifications may be made without departing from the spirit and scope of the present invention.

What is claimed is:

1. A method of making a Hepatitis C virus (HCV) replicon having an increased replication activity in a Huh7 cell or derivative thereof comprising modifying a HCV replicon construct to encode an amino acid substitution at a position corresponding to amino acid 470 of NS3 and to encode an isoleucine at the position corresponding to amino acid 232 of NS5A, using SEQ ID NO: 1 as a reference sequence, wherein a replicon that has been modified has an increased replication activity in said Huh7 cell or derivative thereof compared to said HCV replicon construct prior to said modifying.

2. The method of claim 1, further comprising the step of modifying said HCV replicon construct to encode an amino acid substitution at a position corresponding to amino acid 196 of NS3 using SEQ ID NO: 1 as a reference sequence.

3. The method of claim 1, wherein said amino acid modification is preformed on a replicon construct derived from HCV genotype 1a strain.

4. The method of claim 1, wherein said amino acid modification is preformed on a replicon construct derived from HCV-BK, and said modification results in a methionine at said position corresponding to amino acid 470 of NS3.

5. The method of claim 1, wherein said amino acid modification is preformed on a replicon construct derived from HCV-H77, and said modification results in a leucine at said position corresponding to amino acid 470 of NS3.

6. A method for identifying a Hepatitis C virus (HCV) replicon that grows in cell culture comprising the steps of:
(a) producing a modified replicon construct comprising modifying a HCV replicon construct to encode an amino acid substitution at a position corresponding to amino acid 470 of NS3 and to encode an isoleucine at the position corresponding to amino acid 232 of NS5A, using SEQ ID NO:1 as a reference sequence;
(b) introducing said modified replicon construct into a Huh7 cell or derivative thereof; and
(c) measuring replication activity of said modified replicon construct, wherein increased replication activity as compared to an unmodified HCV replicon indicates the ability of said modified HCV replicon to grow in cell culture.

7. The method of claim 6, wherein said cell is an Huh7 cell.

8. A replicon comprising a nucleotide sequence encoding for SEQ ID NO: 1.

9. The replicon of claim 8, wherein said replicon consists of the nucleic acid sequence of SEQ ID NO: 3.

10. A method of measuring the ability of a compound to affect HCV replicon activity comprising the steps of;
a) providing said compound to a Huh7 cell or derivative thereof comprising a replicon made by the method of claim 1; and
b) measuring HCV replicon activity in said cell in the presence and absence of the compound.

11. A method of measuring the ability of a compound to affect HCV replicon activity comprising the steps of;
a) providing said compound to a Huh7 cell or derivative thereof comprising a replicon made by the method of claim 2; and
b) measuring HCV replicon activity in said cell in the presence and absence of the compound.

12. A method of measuring the ability of a compound to affect HCV replicon activity comprising the steps of;
a) providing said compound to a Huh7 cell or derivative thereof comprising a replicon made by the method of claim 3; and
b) measuring HCV replicon activity in said cell in the presence and absence of the compound.

13. A method of measuring the ability of a compound to affect HCV replicon activity comprising the steps of;
a) providing said compound to a Huh7 cell or derivative thereof comprising a replicon made by the method of claim 4; and
b) measuring HCV replicon activity in said cell in the presence and absence of the compound.

14. A method of measuring the ability of a compound to affect HCV replicon activity comprising the steps of;
a) providing said compound to a Huh7 cell or derivative thereof comprising a replicon made by the method of claim 5; and
b) measuring HCV replicon activity in said cell in the presence and absence of the compound.

15. A method of measuring the ability of a compound to affect HCV replicon activity comprising the steps of;
a) providing said compound to a Huh7 cell or derivative thereof comprising the replicon of claim 8; and
b) measuring HCV replicon activity in said cell in the presence and absence of the compound.

16. A method of measuring the ability of a compound to affect HCV replicon activity comprising the steps of;
a) providing said compound to a Huh7 cell or derivative thereof comprising the replicon of claim 9; and
b) measuring HCV replicon activity in said cell in the presence and absence of the compound.

17. A replicon comprising a nucleotide sequence encoding for SEQ ID NO: 2.

18. The replicon of claim 17, wherein said replicon consists of the nucleic acid sequence of SEQ ID NO: 4.

* * * * *